United States Patent
Dewey et al.

(10) Patent No.: US 10,736,756 B2
(45) Date of Patent: Aug. 11, 2020

(54) RADIOLUCENT TRIAL

(71) Applicant: Warsaw Orthopedic, Inc., Warsaw, IN (US)

(72) Inventors: Jonathan M. Dewey, Memphis, TN (US); William D. Armstrong, Memphis, TN (US); Anthony J. Melkent, Germantown, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 0 days.

(21) Appl. No.: 15/941,463

(22) Filed: Mar. 30, 2018

(65) Prior Publication Data

US 2019/0298545 A1 Oct. 3, 2019

(51) Int. Cl.
| | | |
|---|---|---|
| *A61F 2/46* | (2006.01) | |
| *A61F 2/44* | (2006.01) | |
| *A61B 6/12* | (2006.01) | |
| *A61B 6/00* | (2006.01) | |
| *A61F 2/30* | (2006.01) | |

(52) U.S. Cl.
CPC .............. *A61F 2/4684* (2013.01); *A61B 6/12* (2013.01); *A61B 6/487* (2013.01); *A61F 2/447* (2013.01); *A61F 2/4611* (2013.01); *A61F 2002/3008* (2013.01); *A61F 2002/30168* (2013.01); *A61F 2002/30261* (2013.01); *A61F 2002/30593* (2013.01)

(58) Field of Classification Search
CPC .................................................. A61F 2/4684
See application file for complete search history.

(56) References Cited

U.S. PATENT DOCUMENTS

| | | | |
|---|---|---|---|
| 6,723,097 B2* | 4/2004 | Fraser | A61F 2/4684 |
| | | | 606/247 |
| 7,763,078 B2 | 7/2010 | Peterman et al. | |
| 8,672,948 B2 | 3/2014 | Lemaitre | |
| 9,084,688 B2* | 7/2015 | Hes | A61F 2/4425 |
| 9,139,415 B2 | 9/2015 | Hall et al. | |
| 9,216,098 B2 | 12/2015 | Trudeau et al. | |
| 9,381,098 B2 | 7/2016 | Gittings et al. | |

(Continued)

OTHER PUBLICATIONS

International Search Report and Written Opinion for PCT/US2019/024280, the counterpart application dated Jul. 8, 2019, 10 pages.

*Primary Examiner* — Nicholas J Plionis

(57) ABSTRACT

Spinal implant trials are provided having various configurations and sizes that aid the selection of spinal implants having similar configurations and sizes. A surgeon during surgery can insert various configurations and sizes of the spinal implant trials into a disc space between two adjacent vertebral bodies of a patient to enable the selection of a spinal implant configured and sized to fit the patient's disc space. Fluoroscopic images can be used in aiding the selection of an appropriately configured and sized spinal implant corresponding to one of the spinal implant trials. The spinal implant trials include features that reveal on the fluoroscopic images whether the spinal implant trials are properly oriented and positioned in the disc space. As such, the selection of the configuration and size of the spinal implants can be made after it is determined that the spinal implant trials are properly oriented and positioned within the disc space.

27 Claims, 15 Drawing Sheets

(56) References Cited

U.S. PATENT DOCUMENTS

| | | |
|---|---|---|
| 9,693,882 B2 | 7/2017 | Lomeli et al. |
| 9,730,802 B1 | 8/2017 | Harvey |
| 10,251,759 B2 * | 4/2019 | Butler .................... A61F 2/4465 |
| 2004/0186572 A1 * | 9/2004 | Lange .................... A61F 2/447 623/17.11 |
| 2006/0167461 A1 | 7/2006 | Hawkins et al. |
| 2007/0093898 A1 * | 4/2007 | Schwab ................ A61F 2/4465 623/17.11 |
| 2010/0198263 A1 | 8/2010 | Siegal et al. |
| 2011/0092976 A1 | 4/2011 | Rawles et al. |
| 2014/0277485 A1 * | 9/2014 | Johnson ................ A61F 2/4455 623/17.16 |
| 2014/0330383 A1 * | 11/2014 | Wimberley ........... A61F 2/4611 623/17.16 |
| 2015/0100129 A1 * | 4/2015 | Waugh .................. A61F 2/4455 623/17.16 |
| 2015/0250610 A1 * | 9/2015 | Jacobs ................ A61F 2/30965 623/17.16 |
| 2015/0342757 A1 | 12/2015 | Lomeli et al. |
| 2016/0058571 A1 * | 3/2016 | McLaughlin ........... A61F 2/442 623/17.16 |
| 2016/0113775 A1 * | 4/2016 | Willis .................... A61F 2/442 623/17.16 |
| 2016/0120660 A1 | 5/2016 | Melkent et al. |
| 2016/0262909 A1 | 9/2016 | Lindenmann et al. |
| 2017/0095335 A1 * | 4/2017 | Kieser ...................... A61F 2/30 |
| 2017/0239067 A1 | 8/2017 | Nino |
| 2019/0298546 A1 * | 10/2019 | Dewey .................. A61F 2/4684 |

\* cited by examiner

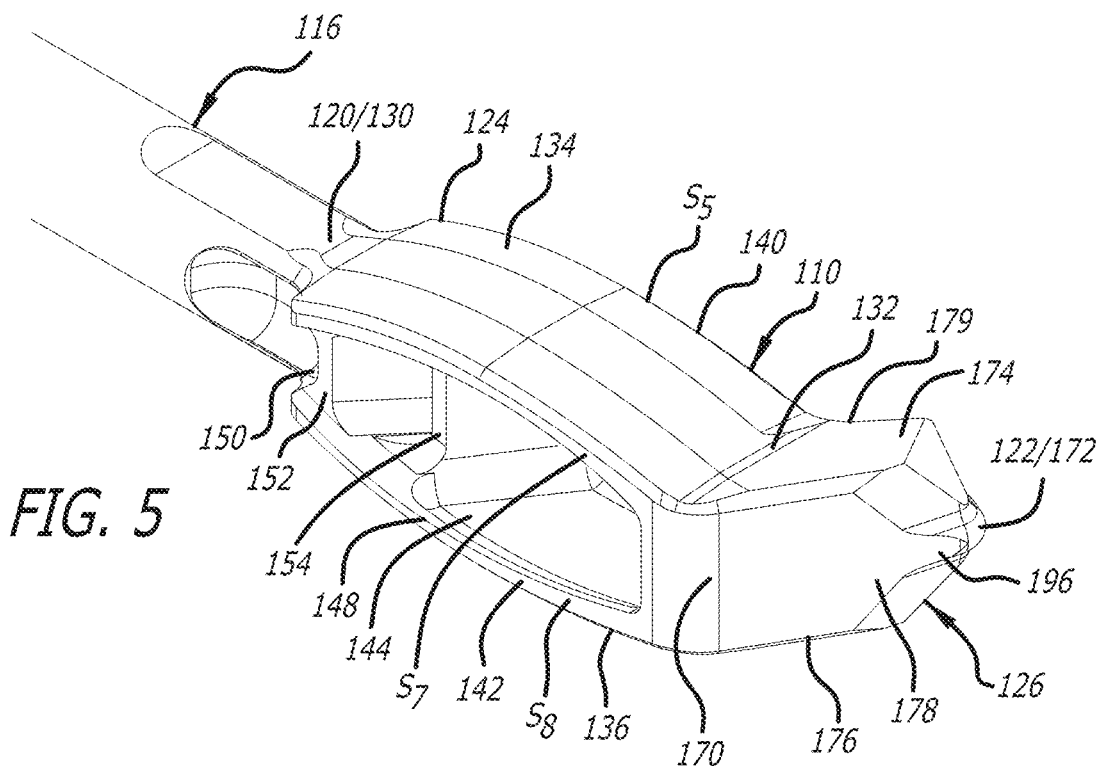

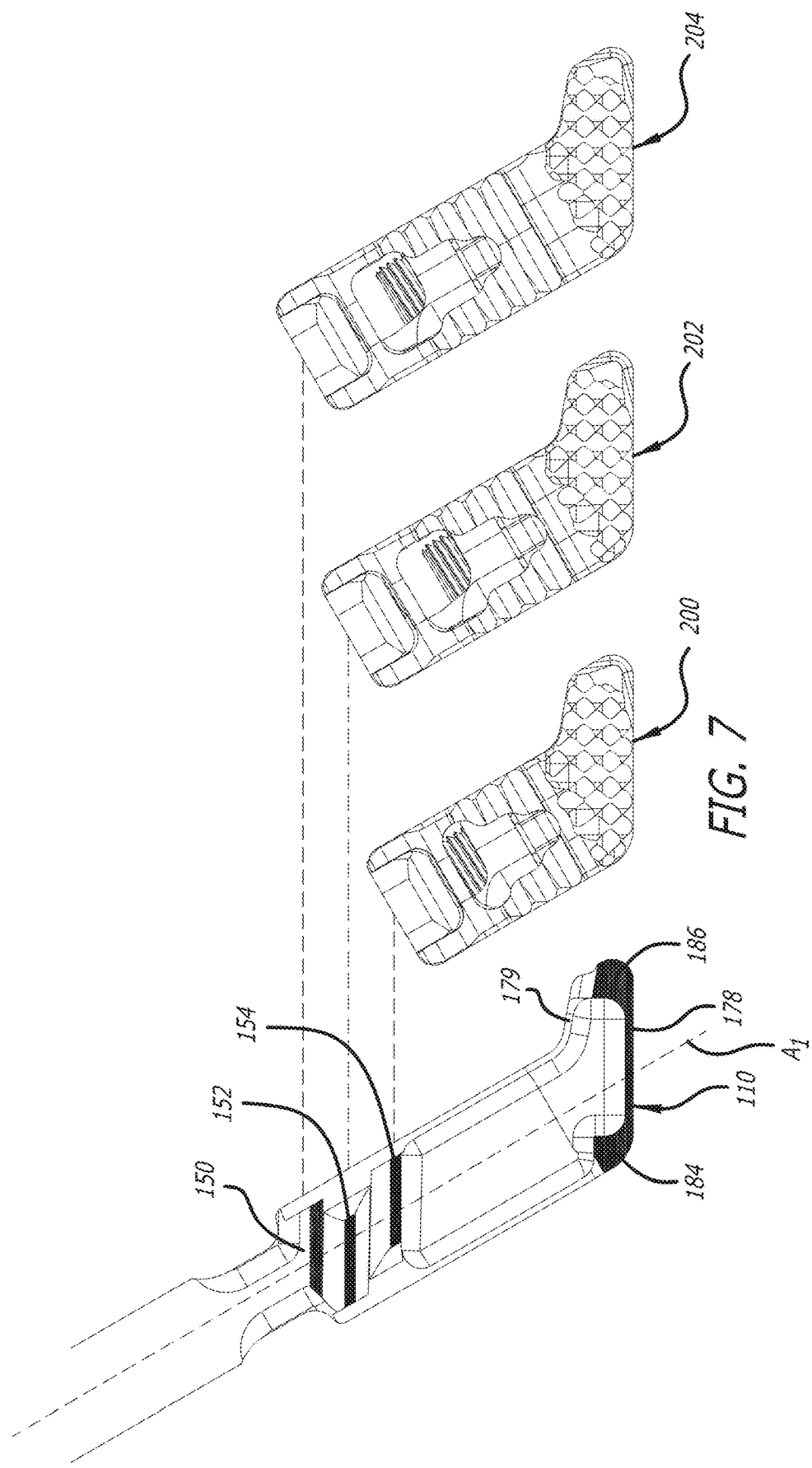

RADIOLUCENT TRIAL

FIELD OF THE INVENTION

The present invention generally relates to a spinal implant trial. More particularly, the present invention relates to a spinal implant trial used to facilitate the selection of appropriately sized interbody spinal fusion implants. More particularly, the present invention relates to a spinal implant trial including features that reveal on fluoroscopic images whether the spinal implant trial is properly oriented and/or positioned in the disc space.

DESCRIPTION OF THE PRIOR ART

Widespread use of interbody spinal fusion implants has been adopted to treat disease of and injuries to the spine. Typically, spinal implant trials are used during surgery to select an appropriately configured and sized spinal fusion implant. Such spinal implant trials correspond to the shapes and dimensions of the spinal fusions available for use. For example, differently shaped and dimensioned spinal implant trials can be sequentially inserted into the disc space during surgery to test for size. Thereafter, a correspondingly shaped and dimensioned spinal fusion implant can be selected for implantation. However, visualization of the disc space in which the spinal fusion interbody is to be implanted is limited during surgery. As such, fluoroscopy can be used at different intervals during surgery to determine the location of spinal implant trials in the disc space. Furthermore, the spinal implant trials can be equipped with radio-opaque markers that can aid the location determination. Nevertheless, because fluoroscopic images are typically only taken from lateral and/or anterior-posterior directions, conventional radio-opaque markers oftentimes do not sufficiently aid in the determination of the orientation and position of the spinal implant trial in the disc space. Therefore, there is a need for a spinal implant trial configured to aid the determination via fluoroscopic imagery of whether the trial is properly oriented and/or positioned in the disc space.

SUMMARY OF THE INVENTION

The present invention in one preferred embodiment contemplates a method of situating a spinal implant trial including providing a spinal implant trial having a proximal first end, a distal second end, a body portion, and a head portion, the body portion extending from the proximal first end to the head portion, and the head portion extending from the body portion to the distal second end, the body portion including a first end collocated with the proximal first end of the spinal implant trial, an opposite second end, a first mid-longitudinal axis extending through the first end and the second end of the body portion, an upper wall portion extending between the first end and the second end of the body portion, a lower wall portion extending between the first end and the second end of the body portion, a first interior portion formed between the upper wall portion and the lower wall portion of the body portion, a first opening provided on a first lateral side of the body portion between the upper wall portion and the lower wall portion of the body portion and communicating with the first interior portion, a second opening provided on a second lateral side of the body portion between the upper wall portion and the lower wall portion of the body portion and communicating with the first interior portion, and at least a first fin provided in the first interior portion, the first fin being at least in part radio opaque, the first fin having a first planar surface in a first plane and a second planar surface in a second plane, the first planar surface and the second planar surface being opposite from and substantially parallel to one another and having a first thickness therebetween, each of the first planar surface and the second planar surface extending from at least adjacent the upper wall portion of the body portion to at least adjacent the lower wall portion of the body portion, and extending from at least adjacent the first opening to at least adjacent the second opening, and the head portion including a first end, an opposite second end collocated with the distal second end of the spinal implant trial, a second mid-longitudinal axis extending through the first end and the second end of the head portion, and an end wall portion positioned at least adjacent the distal second end of the spinal implant trial, the end wall portion including and extending between a first end portion and a second end portion, the first end portion and the second end portion being spaced apart from one another, the first end portion of the end wall portion being positioned proximate the first end of the head portion and the second end portion of the end wall portion being positioned proximate the second end of the head portion, the first end portion and the second end portion of the end wall portion each having a thickness greater than the remainder of the end wall portion and being at least in part radio opaque; inserting the spinal implant trial into a disc space between an upper vertebral body and a lower vertebral body to contact a portion of the upper wall portion with a lower endplate of the upper vertebral body and to contact a portion of the lower wall portion with an upper endplate of the lower vertebral body; orienting the spinal implant trial so that a first horizontal distance across the first fin approximates the first thickness between the first planar surface and the second planar surface of the first fin in at least a first fluoroscopic image from a direct lateral direction to properly orient the spinal implant trial within the disc space by; and positioning the spinal implant trial so that the first end portion and the second end portion of the end wall portion are positioned on opposite sides of a spinous process associated with the upper vertebral body in at least a second fluoroscopic image from an anterior-posterior direction to properly position the spinal implant with respect to the lateral width of the disc space.

The present invention in another preferred embodiment contemplates a method of situating a spinal implant trial including inserting a spinal implant trial from an at least partially posterior direction into a disc space between an upper vertebral body and a lower vertebral body, the spinal implant trial including an interior void extending therethrough that is open along a majority of a first lateral side and a second lateral side of the spinal implant trial, the interior void being interrupted by at least a first fin and defined at one end by an end wall portion of the spinal implant trial, the first fin being at least in part radio opaque, the first fin having a first planar surface in a first plane and a second planar surface in a second plane, the first planar surface and the second planar surface being opposite from and substantially parallel to one another and having a first thickness therebetween, and the end wall portion including and extending between a first end portion and a second end portion, the first end portion and the second end portion being at least in part radio opaque, the first end portion and the second end portion being spaced apart from one another, and each of the first end portion and the second end portion having a thickness greater than the remainder of the end wall portion; contacting an upper wall portion of the spinal implant trial with a lower end portion of the upper vertebral body and contacting a lower wall portion of the spinal implant trial with an upper end portion of the lower vertebral body; placing the spinal implant trial in a first orientation and a first position within the disc space, a substantial majority of the spinal implant trial being positioned on only one lateral side of the disc space; producing a first one of at least two first fluoroscopic images from a direct lateral direction of the spinal implant trial in the first orientation and the first position within the disc space; producing a first one of at least two second fluoroscopic images from an anterior-posterior direction of the spinal implant trial in the first orientation and the first position within the disc space; adjusting the orientation of the spinal implant trial to place the spinal implant trial in a second orientation so that a first horizontal distance across the first fin in a second one of the at least two first fluoroscopic images approximates the first thickness between the first planar surface and the second planar surface of the first fin; and adjusting the position of the spinal implant trial to place the spinal implant trial in a second position so that the first end portion and the second end portion of the end wall portion are positioned on opposite sides of the a spinous process associated with the upper vertebral body in a second one of the at least two second fluoroscopic images.

The present invention in yet another preferred embodiment contemplates a spinal implant trial including a proximal first end, a distal second end, a body portion, and a head portion, the body portion extending from the proximal first end to the head portion, and the head portion extending from the body portion to the distal second end, the body portion including a first end collocated with the proximal first end of the spinal implant trial, an opposite second end, a first mid-longitudinal axis extending through the first end and the second end of the body portion, an upper wall portion extending between the first end and the second end of the body portion, a lower wall portion extending between the first end and the second end, a first interior portion formed between the upper wall portion and the lower wall portion of the body portion, a first opening provided on a first lateral side of the body portion between the upper wall portion and the lower wall portion of the body portion and communicating with the first interior portion, a second opening provided on a second lateral side of the body portion between the upper wall portion and the lower wall portion of the body portion and communicating with the first interior portion, and at least a first fin provided in the first interior portion, the first fin being at least in part radio opaque, the first fin having a first planar surface in a first plane and a second planar surface in a second plane, the first planar surface and the second planar surface being opposite from and substantially parallel to one another and having a first thickness therebetween, each of the first planar surface and the second planar surface extending from at least adjacent the upper wall portion of the body portion to at least adjacent the lower wall portion of the body portion, and extending from at least adjacent the first opening to at least adjacent the second opening, the head portion including a first end, an opposite second end collocated with the distal second end of the spinal implant trial, a second mid-longitudinal axis extending through the first end and the second end of the head portion, an upper wall portion extending between the first end and the second end of the head portion, a lower wall portion extending between the first end and the second end of the head portion, a second interior portion communicating with the first interior portion and formed between the upper wall portion and the lower wall portion of the head portion, and an end wall portion positioned at least adjacent the distal second end of the spinal implant trial, the end wall portion including and extending between a first end portion and a second end portion, the first end portion and the second end portion being spaced apart from one another, the first end portion of the end wall portion being positioned proximate the first end of the head portion and the second end portion of the end wall portion being positioned proximate the second end of the head portion, the first end portion and the second end portion of the end wall portion each having a thickness greater than the remainder of the end wall portion and being at least in part radio opaque, the spinal implant trial defining an empty void between the first fin and the end wall portion across the first interior portion and the second interior portion, where the spinal implant trial is configured for insertion into a disc space between an upper vertebral body and a lower vertebral body, and after insertion into the disc space, fluoroscopic imagery can be used from a direct lateral direction and an anterior-posterior direction to determine if the spinal implant trial is at least properly oriented and properly positioned with respect to the lateral width of the disc space, the fluoroscopic imagery from the direct lateral direction showing that the spinal implant trial is properly oriented within the disc space when the first end portion and the second end portion are substantially aligned with one another, when a first horizontal distance across the first fin approximates the first thickness between the first planar surface and the second planar surface of the first fin, and when a second horizontal distance between the first fin and the first end portion and the second end portion aligned with one another is maximized across the empty void of the first interior portion and the second interior portion, and the fluoroscopic imagery from the anterior-posterior direction showing that the spinal implant trial is properly positioned with respect to the lateral width of the disc space when the first end portion and the second end portion of the end wall portion are positioned on opposite sides of the a spinous process associated with the upper vertebral body.

BRIEF DESCRIPTION OF THE DRAWINGS

FIG. 5 is an enlarged top front perspective view of the spinal implant trial of FIG. 4;

FIG. 6 is an enlarged cutaway view of FIG. 5 depicting the spinal implant trial of FIG. 4;

FIG. 7 is top plan view of the spinal implant trial of FIG. 4 and three sizes of spinal implants for which the spinal implant trial is used to facilitate selection thereof;

DETAILED DESCRIPTION OF THE PREFERRED EMBODIMENT

Figure 1:
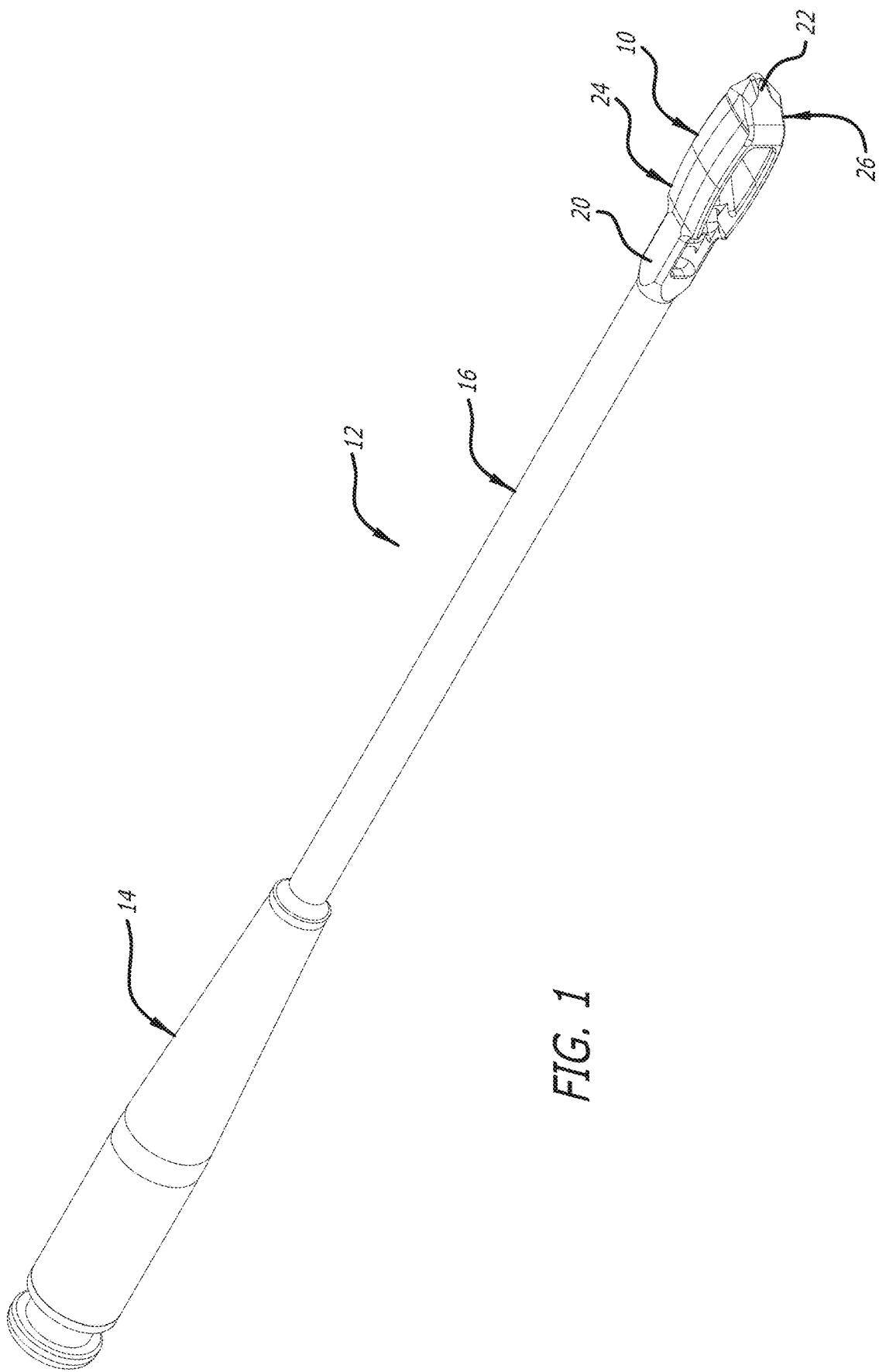
FIG. 1 is a top front perspective view of an instrument including a spinal implant trial according to a first embodiment of the present invention.
Figure 2:
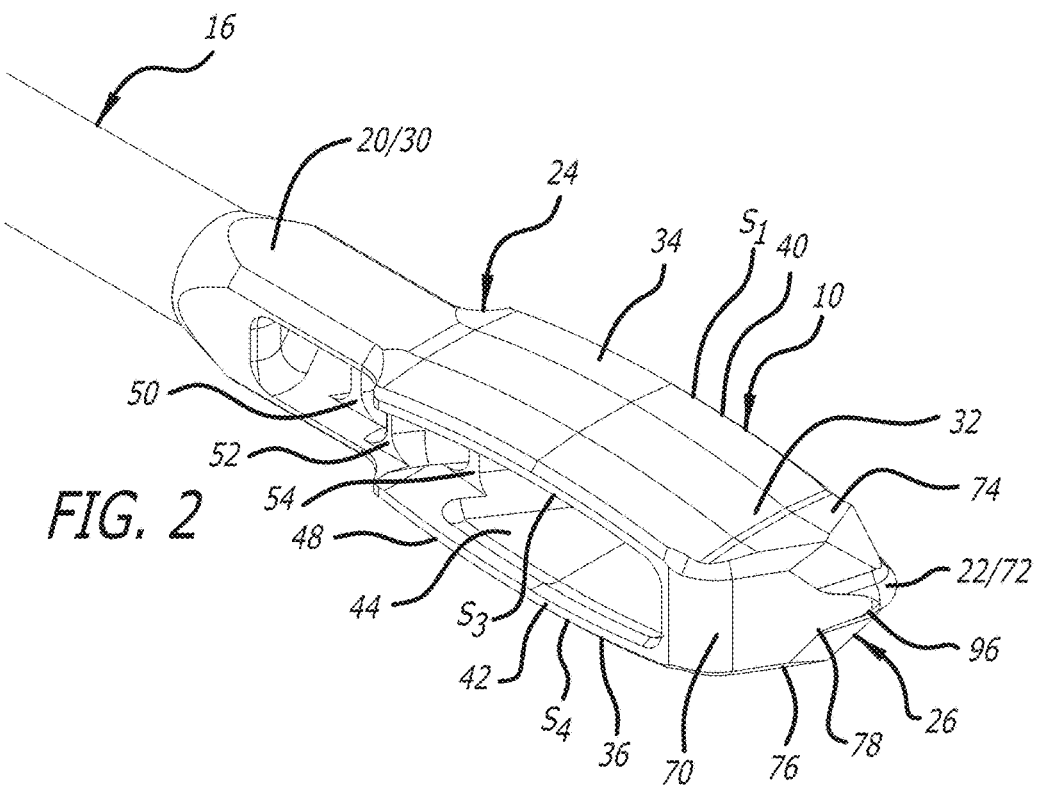
FIG. 2 is an enlarged top front perspective view of the spinal implant trial of FIG. 1.
Figure 3:
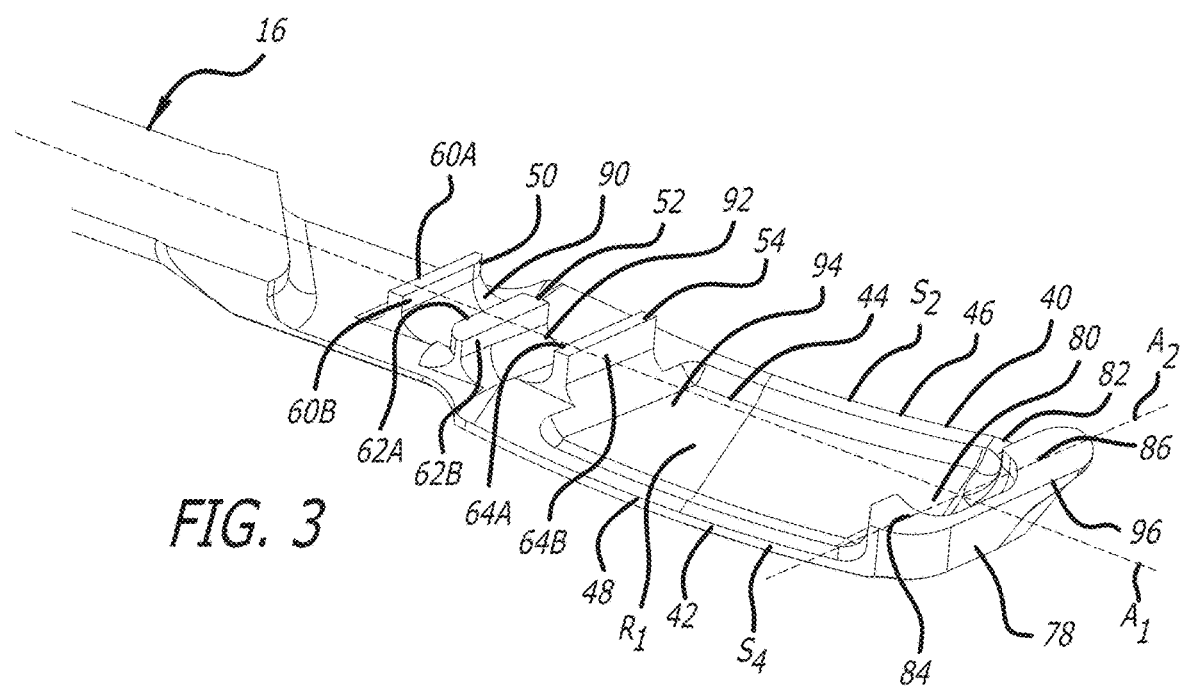
FIG. 3 is an enlarged cutaway view of FIG. 2 depicting the spinal implant trial of FIG. 1.

A spinal implant trial according to one embodiment of the present invention is generally referenced by the numeral 10 in FIGS. 1-3, and a spinal implant trial according to another embodiment of the present invention is generally referenced by the number 110 in FIGS. 4-21. The spinal implant trials 10 and 110 can be formed of materials such as carbon steel, stainless steel, titanium, cobalt chrome, PEEK, tantalum, or any combination of these. The spinal implant trials 10 and 110 can have various sizes corresponding to spinal implants having similar configurations and sizes. As such, a surgeon during surgery can insert various configurations and sizes of the spinal implant trials into a disc space between two adjacent vertebral bodies of a patient to enable the selection of a spinal implant configured and sized to fit the patient's disc space. As discussed below, the spinal implant trials 10 and 110 can also include features that afford selection of appropriately-sized spinal implants.

Fluoroscopy is typically used throughout surgery to aid the selection of an appropriately configured and sized spinal implant. After insertion of one of the spinal implant trials 10 and 110 into the disc space, a fluoroscope can be used to generate fluoroscopic images showing the position thereof in the disc space. Multiple fluoroscopic images from different directions can be generated periodically throughout the surgery to show advancement into and the position of the spinal implant trials 10 and 110 in the disc space. For example, fluoroscopic images from anterior-posterior directions and fluoroscopic images from lateral directions can be generated.

The fluoroscopic images can be used in selecting an appropriately configured and sized spinal implant corresponding to one of the spinal implant trials 10 and 110. Furthermore, the spinal implant trials 10 and 110 include features that reveal on the fluoroscopic images whether the spinal implant trials 10 and 110 are properly oriented and positioned in the disc space. Using the fluoroscopic images and the features thereof, the spinal implant trials 10 and 110 can be properly oriented and positioned within the disc space. As such, the selection of the configuration and size, as well as ideal position in the disc space and implantation trajectory, of the spinal implant or spinal implants can be made after the spinal implant trials 10 and 110 are properly oriented and positioned within the disc space.

As depicted in FIG. 1, the spinal implant trial 10 is included as part of an instrument 12, and the instrument 12 also has a handle 14 and a shaft 16. For example, the spinal implant trial 10 can be removably attached to the shaft 16, so that various sizes of the spinal implant trial 10 can be successively attached to the shaft 16. The surgeon can manipulate the spinal implant trial 10 into position within the disc space via manipulation of the handle 14.

The spinal implant trial 10, as depicted in FIGS. 2 and 3, includes a proximal first end 20 and a distal second end 22. A body portion 24 of the spinal implant trial 10 extends from the proximal first end 20 toward the distal second end 22, and a head portion 26 of the spinal implant trial 10 extends from the body portion 24 to the distal second end 22.

The body portion 24 includes a first end 30, an opposite second end 32, and a mid-longitudinal axis $A_1$ extending through the first end 30 and the second end 32. The first end 30 is collocated with the proximal first end 20, and the second end 32 is located adjacent the head portion 26. The body portion 24 includes an upper wall portion 34 and a lower wall portion 36 spaced apart from one another. The upper and lower wall portions 34 and 36 extend between the first end 20 and the second end 32, and between a first lateral side 40 and a second lateral side 42 of the body portion 24. Portions of the upper wall portion 34 and the lower wall portion 36 can be convex, and the convexity can approximate the curvature of the end plates of the two adjacent vertebral bodies.

As depicted in FIG. 2, an interior 44 is formed between the upper wall portion 34 and the lower wall portion 36. Furthermore, a first opening 46 into the interior 44 is formed between the upper wall portion 34 and the lower wall portion 36 at the first lateral side 40, and a second opening 48 into the interior 44 is formed between the upper wall portion 34 and the lower wall portion 36 at the second lateral side 42. The first opening 46 and the second opening 48 serve as large "windows" into and through the interior 44. Much of the interior 44 is open space between the first lateral side 40 and the second lateral side 42, and as such, there is an uninterrupted view, both visually and fluoroscopically, through much of the interior 44 between the first lateral side 40 and the second lateral side 42. Alternatively, the interior 44 could be filled with radiolucent material to fill in the open space, filling in much (if not all) of the first opening 46 and the second opening 48. The presence of the radiolucent material will be used to reinforce the upper wall portion 34 and the lower wall portion 36, and/or to inhibit abrasion of tissues and inhibit tissues from entering the first opening 46 and the second opening 48.

The upper wall portion 34 and the lower wall portion 36 include side surfaces $S_1$ and $S_2$, respectively, along the first lateral side 40 of the body portion 24, and the upper wall portion 34 and the lower wall portion 36 include side surfaces $S_3$ and $S_4$, respectively, along the second lateral side 42 of the body portion 24. As depicted in FIG. 3, the lower wall portion 36 can include a recessed area $R_1$ that increases the dimensions of the interior 44. Although not shown, the upper wall portion 34 similarly can include a recessed area that increases the dimensions of the interior 44. The recessed areas formed in the upper wall portion 34 and the lower wall portion 36 provide for thinner portions of the upper wall portion 34 and the lower wall portion 36 to reduce their radiographic signature and effectively create lip portions on which the side surfaces $S_1$, $S_2$, $S_3$, and $S_4$ are formed. The size of the sides surfaces $S_1$, $S_2$, $S_3$, and $S_4$ can serve to inhibit tissues from entering the first opening 46 and the second opening 48 and reducing abrasion of the tissues thereon.

Portions (if not all) of the side surfaces $S_1$ and $S_2$ reside in a first plane extending parallel to the mid-longitudinal axis $A_1$, and portions (if not all) of the side surfaces $S_3$ and $S_4$ reside in a second plane extending parallel to the mid-longitudinal axis $A_1$. Substantially all (if not all) of the body portion 24 and the head portion 26 reside between the first and second planes.

As depicted in FIGS. 2 and 3, one or more fins entirely or substantially comprised of radio-opaque or substantially radio-opaque material are provided in the interior 44. For example, a first fin 50 is provided in the interior 44 at and adjacent the first end 30 of the body portion 24, a second fin 52 is provided in the interior 44 adjacent the first fin 50, and a third fin 54 is provided in the interior 44 adjacent the second fin 52. The first fin 50, the second fin 52, and the third fin 154 can be formed integrally or separate from the remainder of the spinal implant trial 10. Furthermore, the first fin 50, the second fin 52, and the third fin 54, for example, can be created via machining processes during manufacturing or formed by additive manufacturing processes. As depicted in FIG. 3, the upper bases and lower bases of the first fin 50, the second fin 52, and the third fin 54 include curved transitions or corner rounds into the remainder of the spinal implant trial 10. These transitions may be necessitated by the limitations of machining during manufacturing. However, more abrupt transitions of the first fin 50, the second fin 52, and the third fin 54 into the remainder of the spinal implant trial 10 may desirable and could, for example, be created using additive manufacturing processes. The abrupt transitions could aid in better visualization of the first fin 50, the second fin 52, and the third fin 54.

The first fin 50 includes a first planar surface 60A and an opposite second planar surface 60B, the second fin 52 includes a first planar surface 62A and an opposite second planar surface 62B, and the third fin 54 includes a first planar surface 64A and an opposite second planar surface 64B. Portions of each of the pairs of surfaces, i.e., the first and second surfaces 60A and 60B, the first and second surfaces 62A and 62B, and the first and second surfaces 64A and 64B are formed in substantially parallel planes, and thus, these portions have substantially uniform thicknesses. And the portions formed in parallel planes extend from at least adjacent the upper wall portion 34 to at least adjacent the lower wall portion 36, and extend from at least adjacent the first opening 46 to at least adjacent the second opening 48. The edges of the first fin 50, the second fin 52, and the third fin 54 adjacent the first opening 46 and the second opening 48 can be dulled or rounded to prevent abrasion of tissues thereon. Portions of the first fin 50, the second fin 52, and the third fin 54 can be radio-opaque or substantially radio-opaque. To illustrate, the first fin 50, the second fin 52, and the third fin 54 could be configured to be entirely radio-opaque or substantially radio-opaque only when viewing from the sides thereof, or gradations thereof. Also, in addition to portions thereof being radio-opaque or substantially radio-opaque, portions of the first fin 50, the second fin 52, and the third fin 54 could be radiolucent or substantially radiolucent. For example, the center portions of the first fin 50, the second fin 52, and the third fin 54 could be radiolucent and the remainders thereof could be radio-opaque or substantially radio-opaque. Furthermore, the first fin 50, the second fin 52, and the third fin 54 can be used in properly orienting the spinal implant trial 10 in the disc space, and the first fin 50, the second fin 52, and the third fin 54 can be used in selecting an appropriately sized spinal implant.

The head portion 26 includes a first end 70, an opposite second end 72, and a mid-longitudinal axis $A_2$ extending through the first end 70 and the second end 72. The first end 70 is collocated with a portion of the second end 32 of the body portion 24, and the second end 72 is collocated with the distal second end 22. The mid-longitudinal axis $A_2$ is transverse to the mid-longitudinal axis $A_1$.

The head portion 26 includes an upper wall portion 74, a lower wall portion 76, and an end wall portion 78. The upper wall portion 74 can be formed contiguously and continuously with the upper wall portion 34, and the lower wall portion 76 can be formed contiguously and continuously with the lower wall portion 36. The upper wall portion 74 and the lower wall portion 76 are spaced apart from one another and extend between the first end 70 and the second end 72, and between the second end 32 of the body portion 24 and the end wall portion 78.

As depicted in FIG. 3, an interior 80 is formed between the upper wall portion 74 and the lower wall portion 76. Furthermore, the interior 80 is bordered in part by the end wall portion 78, and the interior 80 is contiguous and continuous with the interior 44 of the body portion 24. Like much of the interior 44, the interior 80 can be open space, or alternatively, the interior 80 can be filled with a radiolucent material. An opening 82 into the interior 80 is formed adjacent the second end 72 of the head portion 26. The opening 82 is formed adjacent the first lateral side 40 of the body portion 24, and the opening 82 can be contiguous and continuous with the opening 46.

The end wall portion 78 includes a first end portion 84 proximate the first end 70 of the head portion 26 and a second end portion 86 proximate the second end 72 of the head portion 26. The first end portion 84 protrudes into portions of the interior 44 and the interior 80, and the second end portion 86 protrudes into portions of the interior 80. The first end portion 84 and the second end portion 86 each have a thickness greater than the remainder of the end wall portion 78. The first end portion 84 and the second end portion 86 can be radio-opaque or substantially radio-opaque. Furthermore, when aligned with one another, the first end portion 84 and the second end portion 86 have approximately the same shape.

As discussed in detail with respect to similar features of the spinal implant trial 110, the first fin 50, the second fin 52, the third fin 54, and the end wall portion 78 can be used to determine whether the spinal implant trial 10 is properly oriented. Furthermore, when the spinal implant trial 10 is properly oriented, the distances between the end wall portion 78, and the first fin 50, the second fin 52, or the third fin 54 can be used to select appropriately sized spinal implants.

In the corresponding portions of the interior 44 and/or the interior 80, a first space 90 is formed between the first fin 50 and the second fin 52, a second space 92 is formed between the second fin 52 and the third fin 54, and a third space 94 is formed between the third fin 54 and the end wall portion 78. Because the first space 90, the second space 92, and the third space 94 are devoid of any interfering material or alternatively, filled with a radiolucent material, the orientations of the first fin 50, the second fin 52, the third fin 54, the first end portion 84, and the second end portion 86 can be clearly seen in fluoroscopic imagery. As discussed in detail with respect to similar features of the spinal implant trial 110, the orientations of the first fin 50, the second fin 52, and the third fin 54, the first end portion 84, and the second end portion 86 can be used to determine whether the spinal implant trial 10 is properly oriented and/or positioned.

The head portion 26 at and adjacent the second end 72 thereof includes an exterior surface 96 that facilitates entry of the spinal implant trial 10 into the disc space. The exterior surface 96 can be formed as a nose portion similar to that disclosed in U.S. Ser. No. 15/818,395, filed Nov. 20, 2017, which is hereby incorporated by referenced in its entirety.

Figure 4:
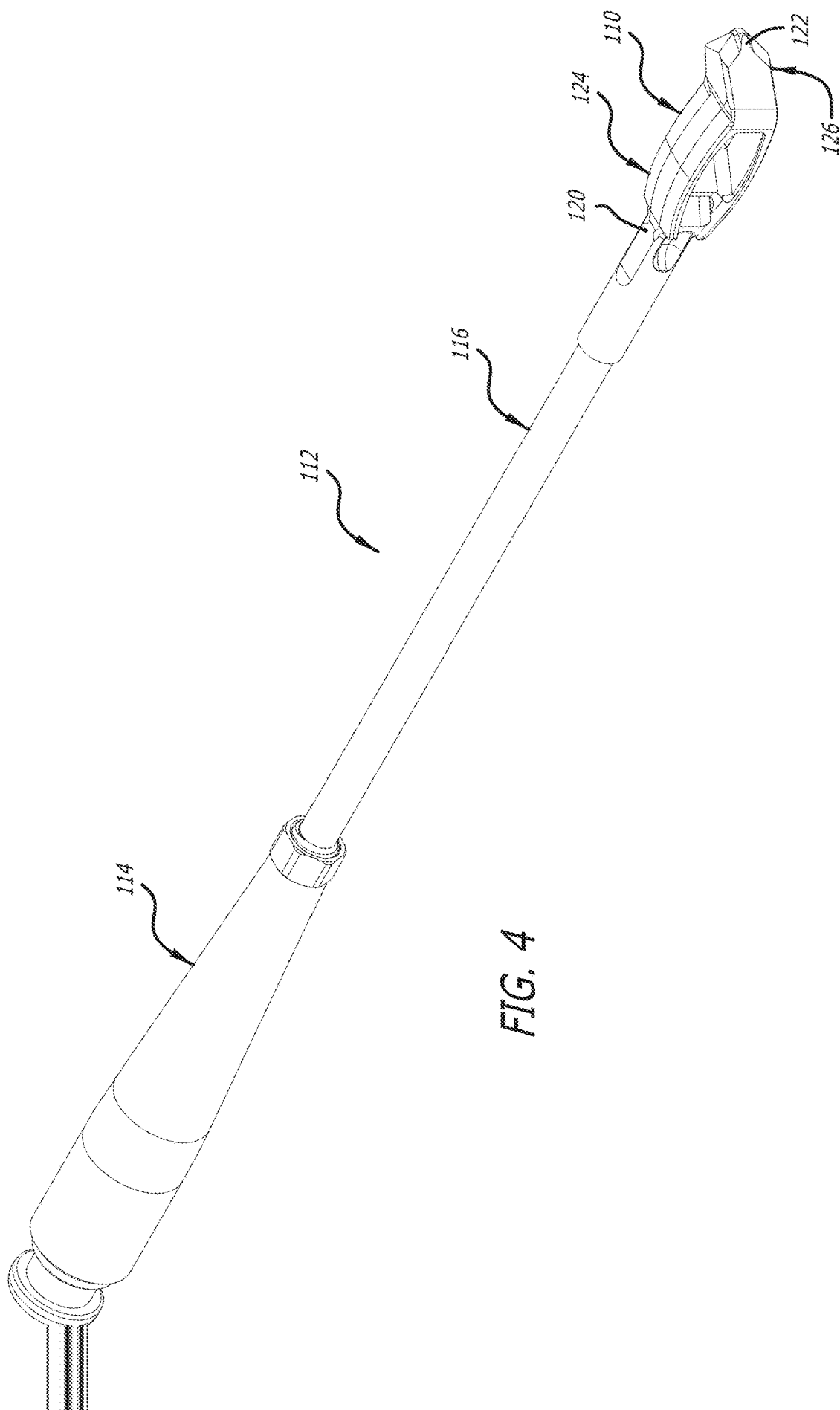
FIG. 4 is a top front perspective view of an instrument including a spinal implant trial according to a second embodiment of the present invention.

As depicted in FIG. 4, the spinal implant trial 110 is included as part of an instrument 112, and the instrument 112 also has a handle 114 and a shaft 116. For example, the spinal implant trial 110 can be removably attached to the shaft 116, so that various sizes of the spinal implant trial 110 can be successively attached to the shaft 116. The surgeon can manipulate the spinal implant trial 110 into position within the disc space via manipulation of the handle 114.

The spinal implant trial 110, as depicted in FIGS. 5 and 6, includes a proximal first end 120 and a distal second end 122. A body portion 124 of the spinal implant trial 110 extends from the proximal first end 120 toward the distal second end 122, and a head portion 126 of the spinal implant trial 110 extends from the body portion 124 to the distal second end 122. As discussed below, unlike the head portion 26 of the spinal implant trial 10, the head portion 126 of the spinal implant trial 110 is extended relative to the body portion 124

The body portion 124 includes a first end 130, an opposite second end 132, and mid-longitudinal axis $A_3$ extending through the first end 130 and the second end 132. The first end 130 is collocated with the proximal first end 120, and the second end 132 is located adjacent the head portion 126. The body portion 124 includes an upper wall portion 134 and a lower wall portion 136 spaced apart from one another and extending between the first end 130 and the second end 132, and between a first lateral side 140 and a second lateral side 142 of the body portion 124. Portions of the upper wall portion 134 and the lower wall portion 136 can be convex, and the convexity can approximate the curvature of the end plates of the two adjacent vertebral bodies.

As depicted in FIG. 5, an interior 144 is formed between the upper wall portion 134 and the lower wall portion 136. Furthermore, a first opening 146 into the interior 144 is formed between the upper wall portion 134 and the lower wall portion 136 at the first lateral side 140, and a second opening 148 into the interior 144 is formed between the upper wall portion 134 and the lower wall portion 136 at the second lateral side 142. The first opening 146 and the second opening 148 serve as large "windows" into and through the interior 144. Much of the interior 144 is open space between the first lateral side 140 and the second lateral side 142, and as such, there is an uninterrupted view, both visually and fluoroscopically, through much of the interior 144 between the first lateral side 140 and the second lateral side 142. Alternatively, the interior 144 could be filled with radiolucent material to fill in the open space, filing in much (if not all) of the first opening 146 and the second opening 148. The presence of the radiolucent material could be used to reinforce the upper wall portion 134 and the lower wall portion 136, and/or to inhibit abrasion of tissues and inhibit tissues from entering the first opening 146 and the second opening 148.

The upper wall portion 134 and the lower wall portion 136 include side surfaces $S_5$ and $S_6$, respectively, along the first lateral side 140 of the body portion 124, and the upper wall portion 134 and the lower wall portion 136 include side surfaces $S_7$ and $S_8$, respectively, along the second lateral side 142 of the body portion 124. As depicted in FIG. 5, the lower wall portion 136 can include a recessed area $R_2$ that increases the dimensions of the interior 144. Although not shown, the upper wall portion 134 similarly can include a recessed area that increases the dimensions of the interior 144. The recessed areas formed in the upper wall portion 134 and the lower wall portion 136 provide for thinner portions of the upper wall portion 134 and the lower wall portion 136 to reduce their radiographic signature and effectively create lip portions on which the side surfaces $S_5$, $S_6$, $S_7$, and $S_8$ are formed. The size of the sides surfaces can serve to inhibit tissues from entering the first opening 146 and the second opening 148 and reducing abrasion of the tissues thereon.

Portions (if not all) of the side surfaces $S_5$ and $S_6$ reside in a third plane extending parallel to the mid-longitudinal axis $A_3$, and portions (if not all) of the side surfaces $S_7$ and $S_8$ reside in a fourth plane extending parallel to the mid-longitudinal axis $A_3$. Substantially all (if not all) of the body portion 124 and portions of the head portion 126 reside between the third and fourth planes.

As depicted in FIGS. 5 and 6, one or more fins of radio-opaque or substantially radio-opaque material are provided in the interior 144. For example, a first fin 150 is provided in the interior 144 at and adjacent the first end 130 of the body portion 124, a second fin 152 is provided in the interior 144 adjacent the first fin 150, and a third fin 154 is provided in the interior 144 adjacent the second fin 152. The first fin 150, the second fin 152, and the third fin 154 can be formed integrally or separate from the remainder of the spinal implant trial 110. Furthermore, the first fin 150, the second fin 152, and the third fin 154, for example, can be created via machining processes during manufacturing or formed by additive manufacturing processes. As depicted in FIG. 6, the upper bases and lower bases of the first fin 150, the second fin 152, and the third fin 154 include curved transitions or corner rounds into the remainder of the spinal implant trial 110. These transitions may be necessitated by the limitations of machining during manufacturing. However, more abrupt transitions of the first fin 150, the second fin 152, and the third fin 154 into the remainder of the spinal implant trial 110 may desirable and could, for example, be created using additive manufacturing processes. The abrupt transitions could aid in better visualization of the first fin 150, the second fin 152, and the third fin 154.

The first fin 150 includes a first planar surface 160A and an opposite second planar surface 160B, the second fin 152 includes a first planar surface 162A and an opposite second planar surface 162B, and the third fin 154 includes a first planar surface 164A and an opposite second planar surface 164B. Portions of each of the pairs of surfaces, i.e., the first and second surfaces 160A and 160B, the first and second surfaces 162A and 162B, and the first and second surfaces 164A and 164B are formed in substantially parallel planes, and thus, these portions have substantially uniform thicknesses. And the portions formed in parallel planes extend from at least adjacent the upper wall portion 134 to at least adjacent the lower wall portion 136, extend from at least adjacent the first opening 146 to at least adjacent the second opening 148. The edges of the first fin 150, the second fin 152, and the third fin 154 adjacent the first opening 146 and the second opening 148 can be dulled or rounded to prevent abrasion of tissues thereon. Portions of the first fin 150, the second fin 152, and the third fin 154 can be radio-opaque or substantially radio-opaque. To illustrate, the first fin 150, the second fin 152, and the third fin 154 could be configured to be entirely radio-opaque or substantially radio-opaque only when viewing from the sides thereof, or gradations thereof. Also, in addition to portions thereof being radio-opaque or substantially radio-opaque, portions of the first fin 150, the second fin 152, and the third fin 154 could be radiolucent or substantially radiolucent. For example, the center portions of the first fin 150, the second fin 152, and the third fin 154 could be radiolucent and the remainders thereof could be radio-opaque or substantially radio-opaque. As discussed below, the first fin 150, the second fin 152, and the third fin 154 can be used in properly orienting the spinal implant trial 110 in the disc space, and the first fin 150, the second fin 152, and the third fin 154 can be used in selecting an appropriately sized spinal implant.

The head portion 126 includes a first end 170, an opposite second end 172, and a mid-longitudinal axis $A_4$ extending through the first end 170 and the second end 172. The first end 170 is collocated with a portion of the second end 132 of the body portion 124, and the second end 172 is collocated with the distal second end 122. The mid-longitudinal axis $A_3$ is transverse to the mid-longitudinal axis $A_4$.

The head portion 126 includes an upper wall portion 174, a lower wall portion 176, an end wall portion 178, and a sidewall portion 179. The upper wall portion 174 can be formed contiguously and continuously with the upper wall portion 134, and the lower wall portion 176 can be formed contiguously and continuously with the lower wall portion 136. The upper wall portion 174 and the lower wall portion 176 are spaced apart from one another and extend between the first end 170 and the second end 172, and between the second end 132 of the body portion 124, the end wall portion 178, and the sidewall portion 179. Unlike the head portion 26 of the spinal implant trial 10, a portion of the head portion 126 extends beyond the third plane. The extended head portion 126 makes the spinal implant trial 110 resemble a hockey-stick.

As depicted in FIG. 6, an interior 180 is formed between the upper wall portion 174 and the lower wall portion 176. Furthermore, the interior 180 is bordered in part by the end wall portion 178, and the interior 180 is contiguous and continuous with the interior 144 of the body portion 124. Like much of the interior 144, the interior 180 can be open space, or alternatively, the interior 180 can be filled with a radiolucent material. An opening 182 into the interior 180 is formed adjacent the second end 172 of the head portion 126. The opening 182 is formed adjacent the first lateral side 140 of the body portion 124, and the opening 182 can be contiguous and continuous with the first opening 146.

Figure 11:
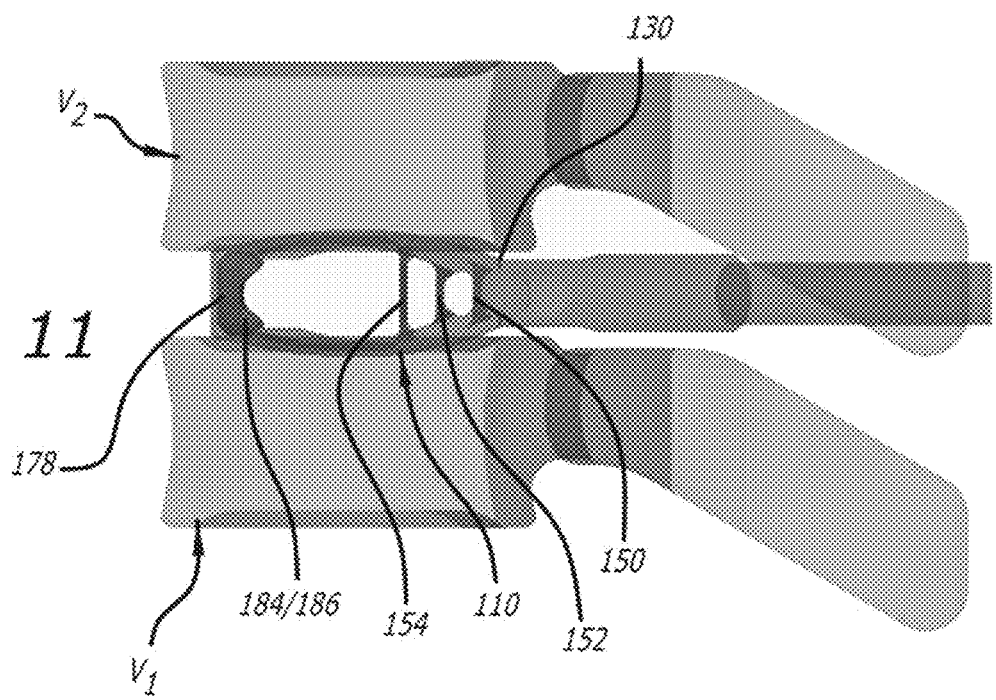
FIG. 11 is a representation of a direct lateral fluoroscopic image of the spinal implant trial of FIG. 4 in the first position in the disc space.

The end wall portion 178 includes a first end portion 184 proximate the first end 170 of the head portion 126 and a second end portion 186 proximate the second end 172 of the head portion 126. The first end portion 184 protrudes into portions of the interior 144 and the interior 180, and the second end portion 186 protrudes into portions of the interior 180. The first end portion 184 and the second end portion 186 each have a thickness greater than the remainder of the end wall portion 178. The first end portion 184 and the second end portion 186 can be radio-opaque or substantially radio-opaque. Furthermore, when aligned with one another, the first end portion 184 and the second end portion 186 have approximately the same shape (FIG. 11).

The first fin 150, the second fin 152, the third fin 154, and the end wall portion 178 can be used to determine whether the spinal implant trial 110 is properly oriented. Furthermore, when the spinal implant trial 110 is properly oriented, the distances between the end wall portion 178, and the first fin 150, the second fin 152, or the third fin 154 can be used to select appropriately sized spinal implants.

In the corresponding portions of the interior 144 and/or the interior 180, a first space 190 is formed between the first fin 150 and the second fin 152, a second space 192 is formed between the second fin 152 and the third fin 154, and a third space 194 is formed between the third fin 154 and the end wall portion 178. Because the first space 190, the second space 192, and the third space 194 are devoid of any interfering material or filled with a radiolucent material, the orientations of the first fin 150, the second fin 152, the third fin 154, the first end portion 184, and the second end portion 186 can be clearly seen in fluoroscopic imagery. The orientations of the first fin 150, the second fin 152, and the third fin 154, the first end portion 184, and the second end portion 186 can be used to determine whether the spinal implant trial 110 is properly oriented and/or positioned.

The head portion 126 at and adjacent the second end 172 thereof includes an exterior surface 196 that facilitates entry of the spinal implant trial 110 into the disc space. The exterior surface 196 can be formed as a nose portion like the nose portion 96.

FIG. 7 depicts a portion of the spinal implant trial 110 showing the first fin 150, the second fin 152, and the third fin 154, and showing the spinal implant trial 110 adjacent a first spinal implant 200, a second spinal implant 202, and a third spinal implant 204. The first spinal implant 200, the second spinal implant 202, and the third spinal implant 204 have similar configurations to the spinal implant trial 110. As depicted in FIG. 7, the placement of the first fin 150 corresponds to the size of the first spinal implant 200, the placement of the second fin 152 corresponds to the size of the second spinal implant 202, and the placement of the third fin 154 corresponds to the size of the third spinal implant 204. The first fin 150, the second fin 152, and the third fin 154 have been darkened for emphasis. The first fin 50, the second fin 52, and the third fin 54 of the spinal implant trial 10 are similarly arranged to correspond to sizes of spinal implants (not shown) having similar configurations as the spinal implant trial 10. As such, when the spinal implant trials 10 and 110 are properly oriented and positioned within the disc space, the proper size of a spinal implant to be used can be determined using the first fin 50, the second fin 52, and the third fin 54, and using the first fin 150, the second fin 152, and the third fin 154. For example, once the spinal implant trials 10 and 110 are properly oriented and positioned, a surgeon could select a spinal implant having a length corresponding to the one of the first fin 50, the second fin 52, or the third fin 54 or the one of the first fin 150, the second fin 152, or the third fin 154 that is aligned with the posterior rims of the vertebral bodies.

The spinal implant trials 10 and 110 can be used in a variety of spinal implant procedures to facilitate the selection of the configuration and size, as well as ideal position in the disc space and implantation trajectory, of the spinal implant or spinal implants ultimately used. For example, the spinal implant trials 10 and 110 can be used in TLIF (tranforminal lumbar interbody fusion) and PLIF (posterior lumbar interbody fusion) procedures.

Figure 8:
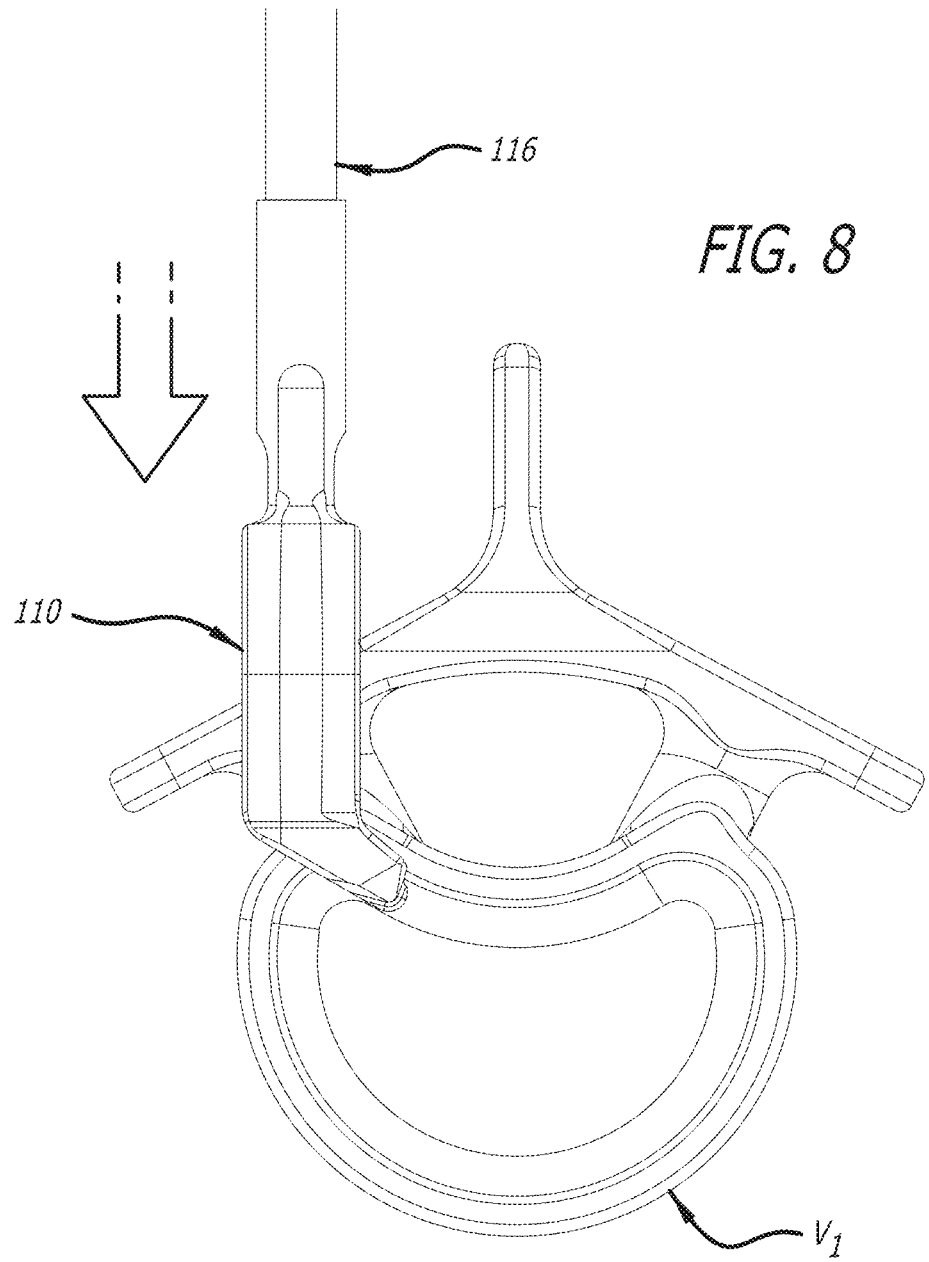
FIG. 8 is a top plan view of the spinal implant trial of FIG. 4 and a lower vertebral body bordering a disc space representing a first step of the surgical insertion of the spinal implant trial into the disc space.
Figure 9:
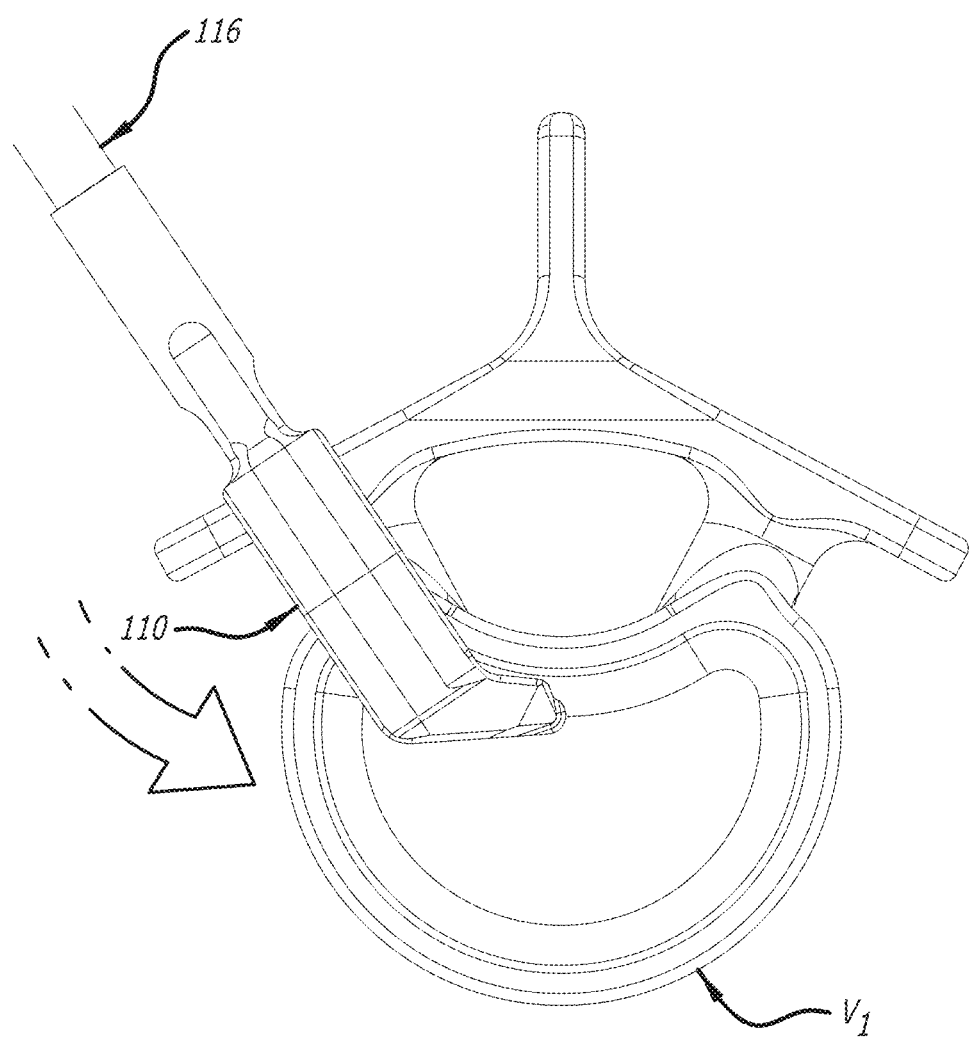
FIG. 9 is a top plan view of the spinal implant trial of FIG. 4 and the lower vertebral body bordering the disc space representing a second step of the surgical insertion of the spinal implant trial into the disc space.

FIGS. 8-10, 13, 16, 19 are top plan views of the spinal implant trial 110 with respect to a lower vertebral body $V_1$ to illustrate the insertion of the spinal implant trial 110 into the disc space. FIGS. 8 and 9 show the initial insertion of the spinal implant trial 110 into the disc space from a posterior approach to the spine. After the initial insertion depicted in FIG. 8, the spinal implant trial 110 can be rotated during further insertion as depicted in FIG. 9. Thereafter, the spinal implant trial 110 can be further inserted into the disc space as depicted in FIGS. 10, 13, 16, and 19. Using fluoroscopy, images taken from lateral and/or anterior-posterior directions (FIGS. 11, 12, 14, 15, 17, 18, 20, and 21) and the features of the spinal implant trial 110 depicted in the fluoroscopic images can be used to determine whether the spinal implant trial 110 is properly oriented and positioned in the disc space between the lower vertebral body $V_1$ and an upper vertebral body $V_2$. The spinal implant trial 110 can be positioned and repositioned to provide for the proper orientation and position as determined by fluoroscopy and the features of the spinal implant trial 110. Thereafter, the features of the spinal implant trial 110 can be used to select the configuration and size, as well as ideal position in the disc space and implantation trajectory, of the spinal implant or spinal implants ultimately used.

Figure 10:
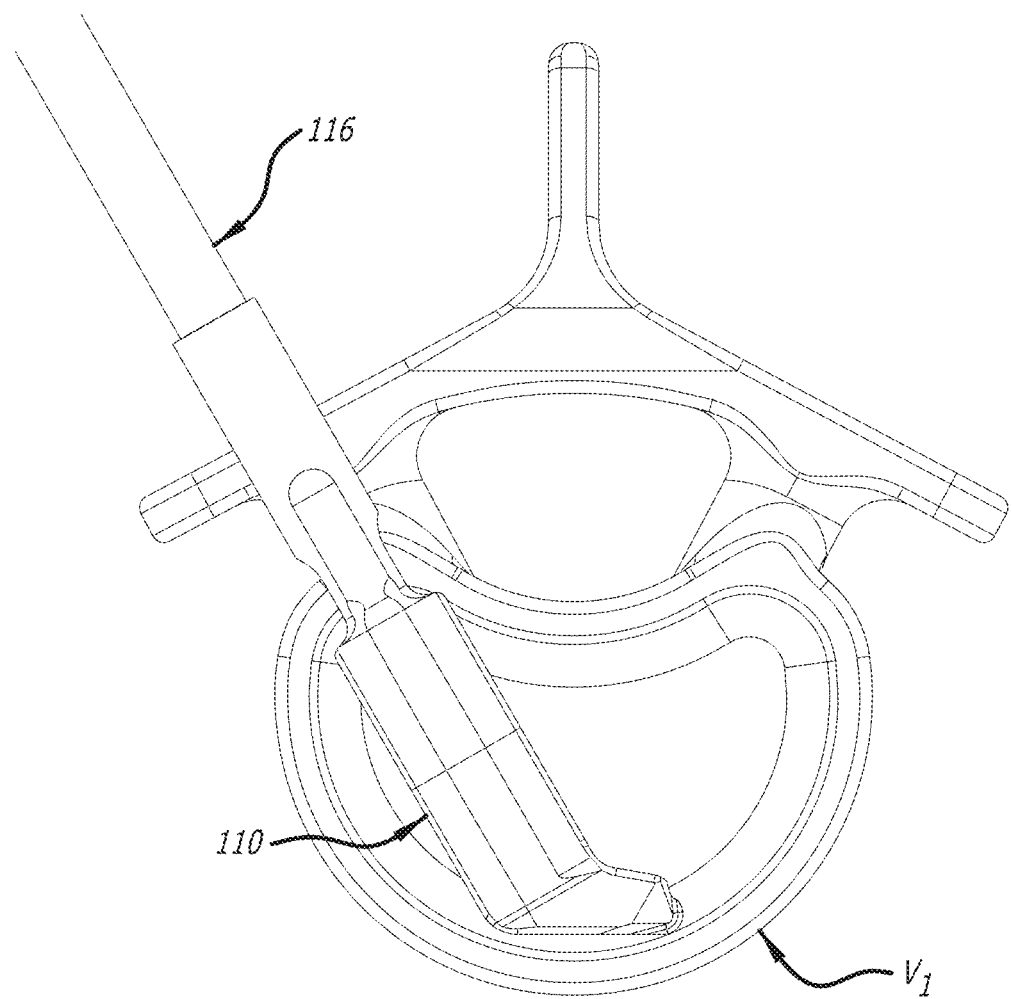
FIG. 10 is a top plan view of the spinal implant trial of FIG. 4 and the lower vertebral body bordering the disc space representing a first position of the spinal implant trial in the disc space.
Figure 12:
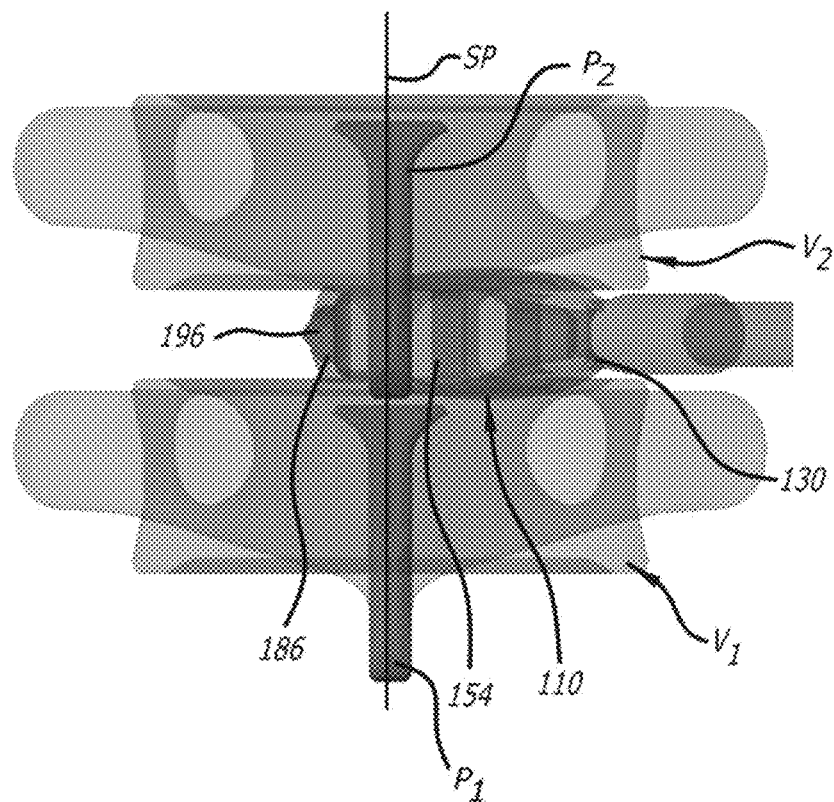
FIG. 12 is a representation of an anterior-posterior fluoroscopic image of the spinal implant trial of FIG. 4 in the first position in the disc space.

FIGS. 11 and 12 are representations of fluoroscopic images taken of the spinal implant trial 110 as positioned in the disc space as shown FIG. 10 from the lateral direction and the anterior-posterior direction, respectively. FIGS. 11 and 12 show the that spinal implant trial 110 is properly oriented and positioned within the disc space between the lower vertebral body $V_1$ and the upper vertebral body $V_2$.

When properly oriented and positioned, the lateral direction fluoroscopic representation depicted in FIG. 11 at the very least does not show the tip of the nose portion 196, shows the first end portion 184 and the second end portion 186 being aligned with one another, shows the first fin 150, the second fin 152, and the third fin 154 having horizontal distances thereacross that approximate the thicknesses between the planar surfaces 160A and 160B, 162A and 162B, and 164A and 164B, and shows the position of the end wall portion 178 being adjacent the anterior edges for the lower vertebral body $V_1$ and the upper vertebral body $V_2$.

Furthermore, when properly oriented and positioned, the anterior-posterior fluoroscopic representation depicted in FIG. 12 at the very least shows the position of the tip of the nose portion 196 spaced slightly apart from the sagittal plane SP and the spinous process $P_2$, the third fin 154 being positioned on an opposite side of the sagittal plane SP and the spinous process $P_2$ from the tip of the nose portion 196, and the position of the end portion 130 being spaced apart from the lateral edges of the lower vertebral body $V_1$ and the upper vertebral body $V_2$.

Figure 13:
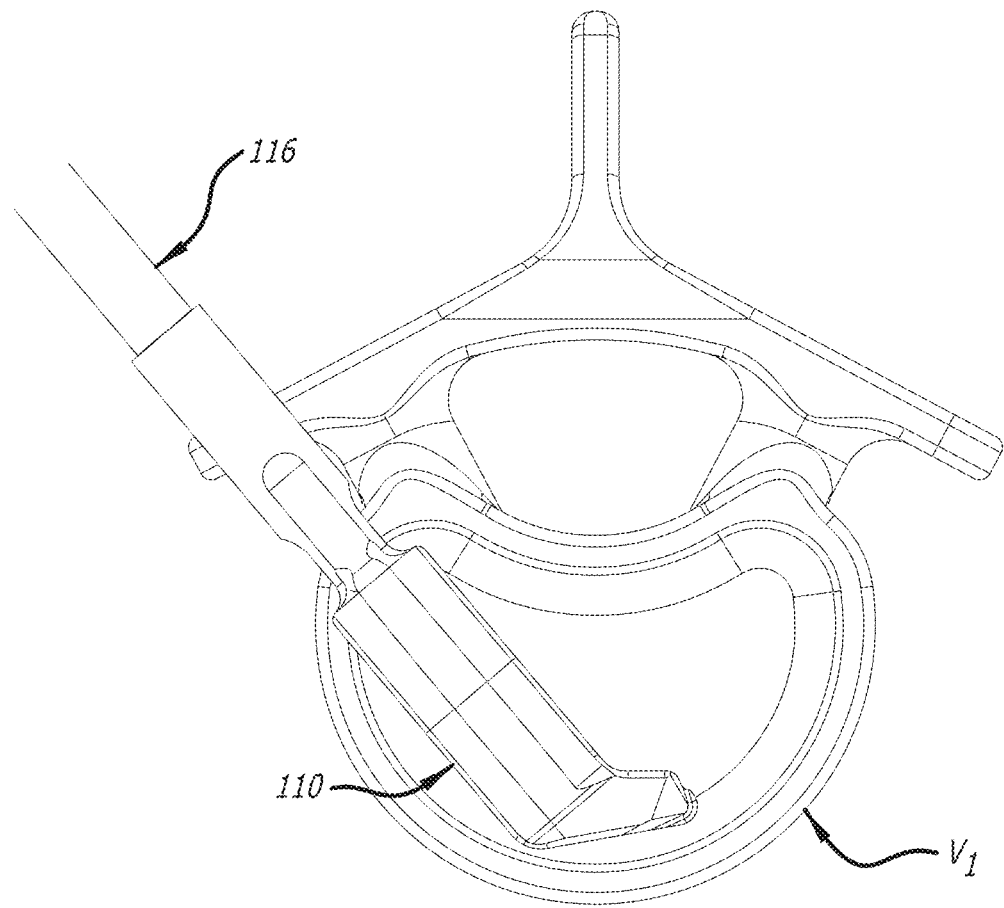
FIG. 13 is a top plan view of the spinal implant trial of FIG. 4 and the lower vertebral body bordering the disc space representing a second position of the spinal implant trial in the disc space.
Figure 14:
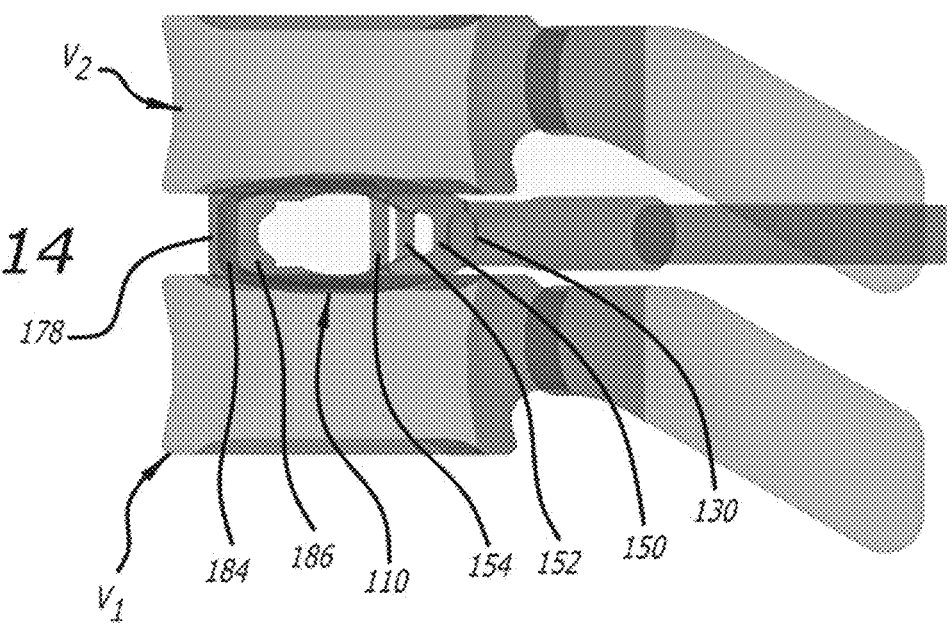
FIG. 14 is a representation of a direct lateral fluoroscopic image of the spinal implant trial of FIG. 4 in the second position in the disc space.
Figure 15:
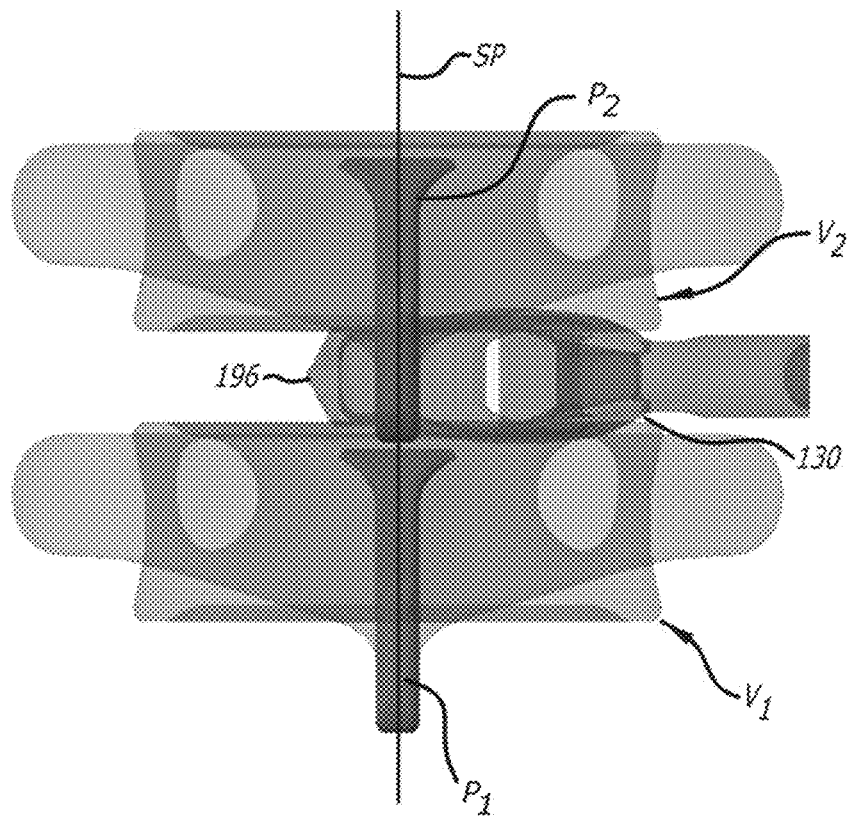
FIG. 15 is a representation of an anterior-posterior fluoroscopic image of the spinal implant trial of FIG. 4 in the second position in the disc space.

FIGS. 14 and 15 are representations of fluoroscopic images taken of the spinal implant trial 110 as positioned in the disc space as shown in FIG. 13 from the lateral direction and the anterior-posterior direction, respectively. FIGS. 14 and 15 show that the spinal implant trial 110 is not properly oriented and positioned within the disc space between the lower vertebral body $V_1$ and the upper vertebral body $V_2$. The improper orientation and position of the spinal implant trial 110 is evidenced at the very least in FIG. 14 by the misalignment of the first end portion 184 and the second end portion 186, and the horizontal distances across the first fin 150, the second fin 152, and the third fin 154 being much greater than the thicknesses between the planar surfaces 160A and 160B, 162A and 162B, and 164A and 164B. Furthermore, the improper orientation and position of the spinal implant trial 110 is evidenced at the very least in FIG. 15 by the position of the end portion 130 being at or immediately adjacent the lateral edges of the lower vertebral body $V_1$ and the upper vertebral body $V_2$.

Figure 16:
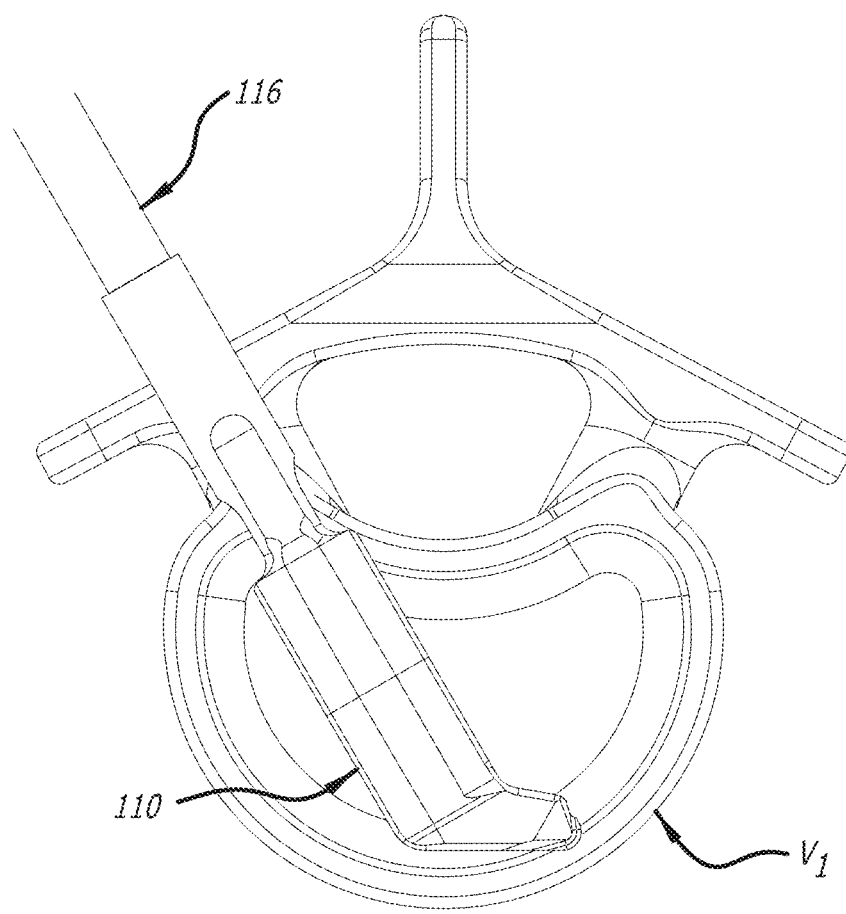
FIG. 16 is a top plan view of the spinal implant trial of FIG. 4 and the lower vertebral body bordering the disc space representing a third position of the spinal implant trial in the disc space.
Figure 17:
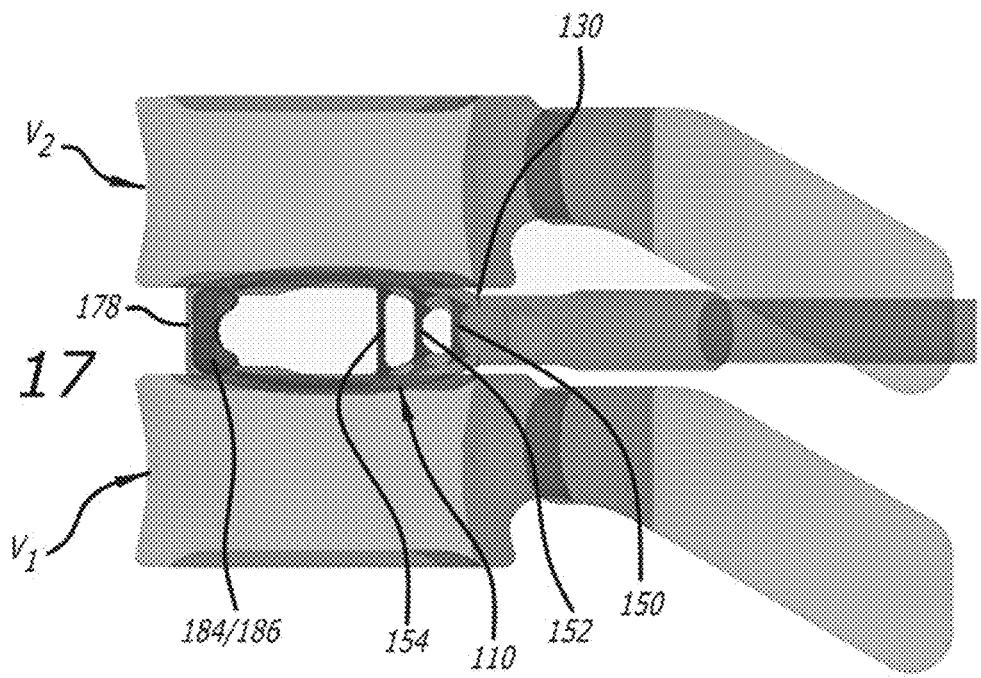
FIG. 17 is a representation of a direct lateral fluoroscopic image of the spinal implant trial of FIG. 4 in the third position in the disc space.
Figure 18:
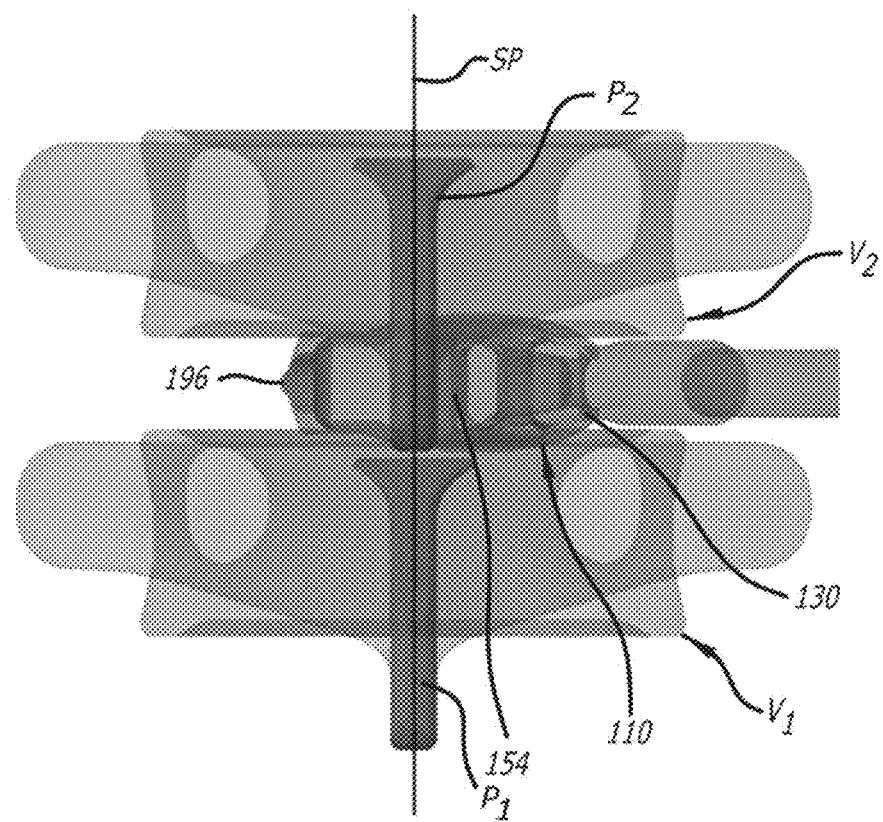
FIG. 18 is a representation of an anterior-posterior fluoroscopic image of the spinal implant trial of FIG. 4 in the third position in the disc space.

FIGS. 17 and 18 are representations of the fluoroscopic images taken of the spinal implant trial 110 as positioned in the disc space as shown in FIG. 16 from the lateral direction and anterior-posterior direction, respectively. While FIG. 17 shows that the spinal implant trial 110 is properly oriented and positioned, FIG. 18 does not. The improper orientation and position of the spinal implant trial 110 is evidenced at the very least in FIG. 18 by the position of the nose portion 196 being spaced too far from the sagittal plane SP and the spinous process $P_2$, and the position of the end portion 130 being spaced too far from the lateral edges of the lower vertebral body $V_1$ and the upper vertebral body $V_2$.

Figure 19:
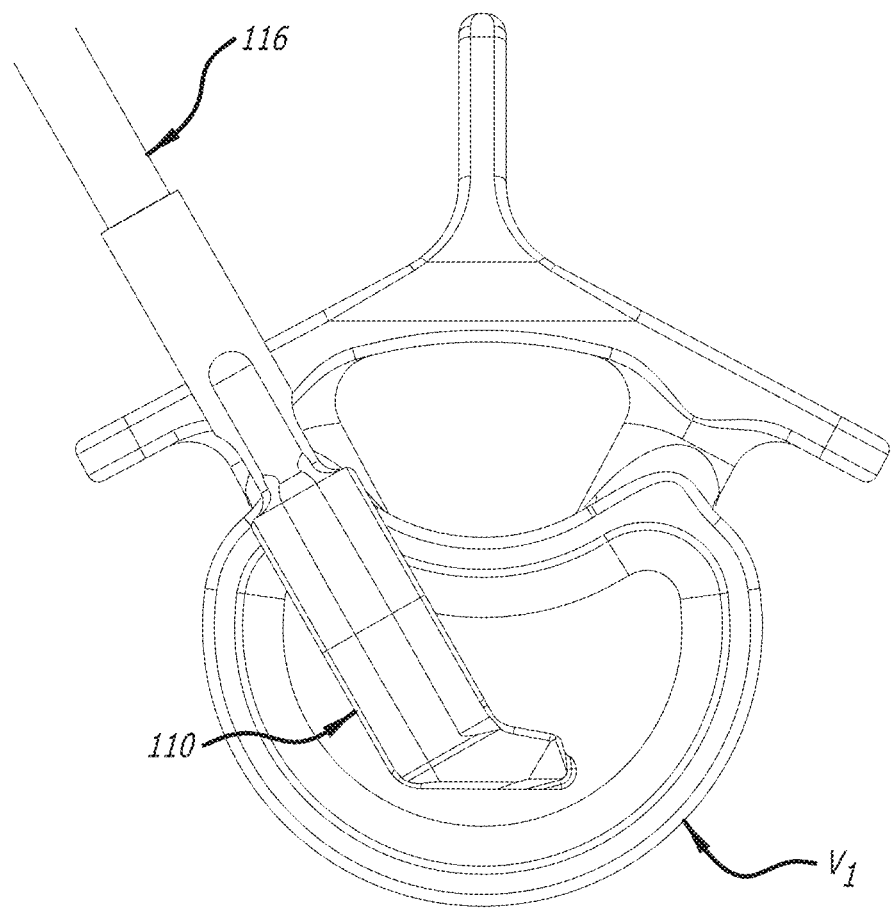
FIG. 19 is a top plan view of the spinal implant trial of FIG. 4 and the lower vertebral body bordering the disc space representing a fourth position of the spinal implant trial in the disc space.
Figure 20:
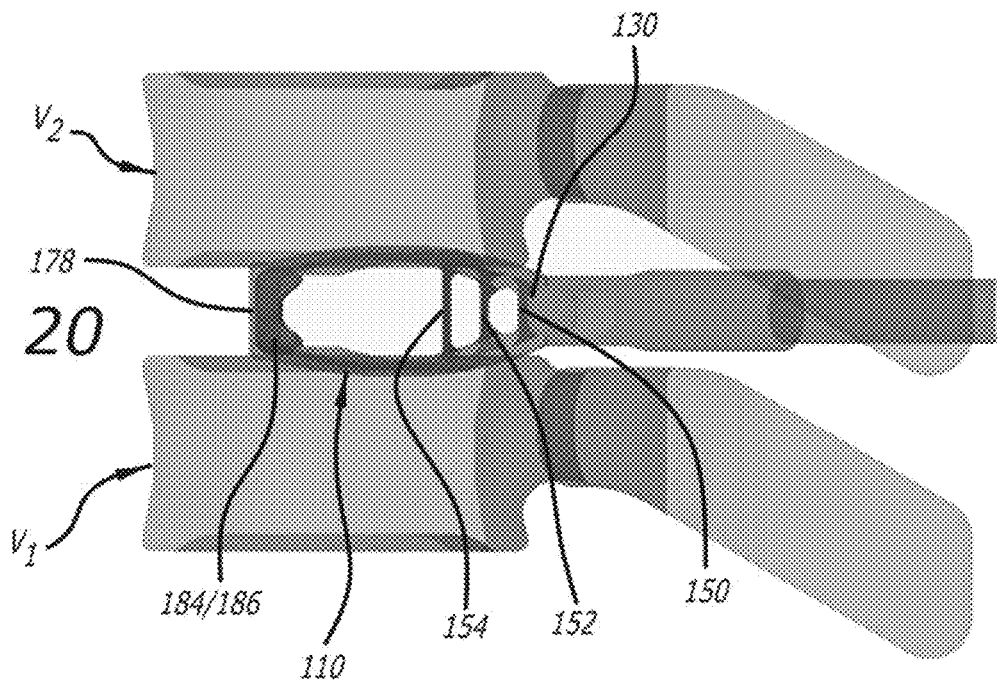
FIG. 20 is a representation of a direct lateral fluoroscopic image of the spinal implant trial of FIG. 4 in the fourth position in the disc space.
Figure 21:
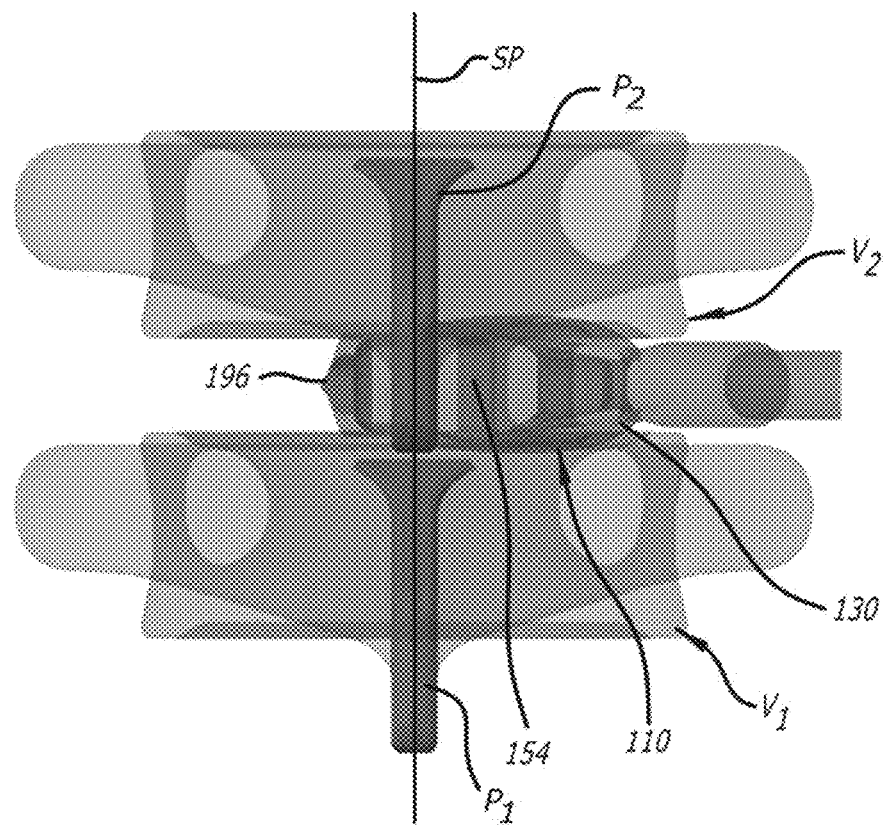
FIG. 21 is a representation of an anterior-posterior fluoroscopic image of the spinal implant trial of FIG. 4 in the fourth position in the disc space.

FIGS. 20 and 21 are representations of the fluoroscopic images taken of the spinal implant trial 110 as positioned in the disc space as shown in FIG. 19 from the lateral direction and anterior-posterior direction, respectively. While FIG. 21 shows that the spinal implant trial 110 is properly oriented and positioned, FIG. 20 does not. The improper orientation and position of the spinal implant trial 110 is evidenced at the very least in FIG. 20 by the position of the end wall portion 178 being spaced too far from the anterior edges of the lower vertebral body $V_1$ and the upper vertebral body $V_2$, and the position of the end portion 130 being at or immediately adjacent the posterior edges of the lower vertebral body $V_1$ and the upper vertebral body $V_2$.

While the spinal implant trial 110 is depicted in FIGS. 8-21, the spinal implant trial 10 can be used in a similar manner. Furthermore, while the spinal implant trials 10 and 110 can be inserted into the disc space from posterior directions, the spinal implant trials 10 and 110 can also be inserted into the disc space from anterior, anterolateral, posterolateral, and lateral directions. By properly orienting and positioning the spinal implant trials 10 and 110 in the disc space, an appropriately configured and sized spinal implant, as well as ideal position in the disc space and implantation trajectory of the spinal implant or spinal implants, can be selected.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of situating a spinal implant trial, the method comprising:
providing a spinal implant trial having a proximal first end, a distal second end, a body portion, and a head portion, the body portion extending from the proximal first end to the head portion, and the head portion extending from the body portion to the distal second end, the body portion including a first end collocated with the proximal first end of the spinal implant trial, an opposite second end, a first mid-longitudinal axis extending through the first end and the second end of the body portion, an upper wall portion extending between the first end and the second end of the body portion, a lower wall portion extending between the first end and the second end of the body portion, a first interior portion formed between the upper wall portion and the lower wall portion of the body portion, a first opening provided on a first lateral side of the body portion between the upper wall portion and the lower wall portion of the body portion and communicating with the first interior portion, a second opening provided on a second lateral side of the body portion between the upper wall portion and the lower wall portion of the body portion and communicating with the first interior portion, and at least a first fin provided in the first interior portion, the first fin being at least in part radio opaque, the first fin having a first planar surface in a first plane and a second planar surface in a second plane, the first planar surface and the second planar surface being opposite from and aligned with one another and having a first maximum thickness therebetween, each of the first planar surface and the second planar surface extending from at least adjacent the upper wall portion of the body portion to at least adjacent the lower wall portion of the body portion, and extending from at least adjacent the first opening to at least adjacent the second opening, and the head portion including a first end, an opposite second end collocated with the distal second end of the spinal implant trial, a second mid-longitudinal axis extending through the first end and the second end of the head portion, and an end wall portion positioned at least adjacent the distal second end of the spinal implant trial, the end wall portion including and extending between a first end portion and a second end portion, the first end portion and the second end portion being spaced apart from one another, the first end portion of the end wall portion being positioned proximate the first end of the head portion and the second end portion of the end wall portion being positioned proximate the second end of the head portion, the first end portion and the second end portion of the end wall portion each having a thickness greater than the remainder of the end wall portion and being at least in part radio opaque;
  inserting the spinal implant trial into a disc space between an upper vertebral body and a lower vertebral body to contact a portion of the upper wall portion with a lower endplate of the upper vertebral body and to contact a portion of the lower wall portion with an upper endplate of the lower vertebral body;
  orienting the spinal implant trial so that a first horizontal distance across the first fin approximates the first maximum thickness between the first planar surface and the second planar surface of the first fin in at least a first fluoroscopic image from a direct lateral direction to properly orient the spinal implant trial within the disc space by; and
  positioning the spinal implant trial so that the first end portion and the second end portion of the end wall portion are positioned on opposite sides of a spinous process associated with the upper vertebral body in at least a second fluoroscopic image from an anterior-posterior direction to properly position the spinal implant with respect to the lateral width of the disc space.

2. The method of claim 1, further comprising orienting the spinal implant trial so that the first end portion and the second end portion of the end wall portion are overlapped with one another in the at least a first fluoroscopic image to properly orient the spinal implant trial within the disc space.

3. The method of claim 2, further comprising orienting the spinal implant trial so that a second horizontal distance in the at least a first fluoroscopic image between the first fin, and the first end portion and the second end portion that are overlapped with one another is maximized to properly orient the spinal implant within the disc space.

4. The method of claim 1, wherein the body portion further includes a second fin provided in the first interior portion, the second fin being positioned between the first end of the body portion and the first fin in the first interior portion, the second fin having a third planar surface in a third plane and a fourth planar surface in a fourth plane, the third planar surface and the fourth planar surface being opposite from and aligned with one another and having a second maximum thickness therebetween, each of the third planar surface and the fourth planar surface extending from at least adjacent the first opening to at least adjacent the second opening, and extending between the upper wall portion and the lower wall portion of the body portion within the first interior space.

5. The method of claim 4, further comprising orienting the spinal implant trial so that a second horizontal distance across the second fin approximates the second maximum thickness between the third planar surface and the fourth planar surface of the second fin in at least the first fluoroscopic image to properly orient the spinal implant trial within the disc space.

6. The method of claim 4, further comprising selecting a spinal implant corresponding to one of a second horizontal distance in the at least a first fluoroscopic image between the first fin, and the first end portion and the second end portion that are overlapped with one another, and a third horizontal distance in the at least a first fluoroscopic image between the second fin, and the first end portion and the second end portion that are overlapped with one another.

7. The method of claim 1, wherein the first mid-longitudinal axis and the second mid-longitudinal axis are transverse to one another, the upper wall portion and the lower wall portion each include a first side surface extending at least partially in a third plane parallel to the mid-longitudinal axis, and the upper wall portion and the lower wall portion each include a second side surface extending at least partially in a fourth plane parallel to the mid-longitudinal axis, the body portion residing between the third plane and the fourth plane, and a portion of the head portion being located on an opposite side of the third plane from the body portion.

8. A method of situating a spinal implant trial, the method comprising:
  inserting a spinal implant trial from an at least partially posterior direction into a disc space between an upper vertebral body and a lower vertebral body, the spinal implant trial including an interior void extending therethrough that is open along a majority of a first lateral side and a second lateral side of the spinal implant trial, the interior void being interrupted by at least a first fin and defined at one end by an end wall portion of the spinal implant trial, the first fin being at least in part radio opaque, the first fin having a first planar surface in a first plane and a second planar surface in a second plane, the first planar surface and the second planar surface being opposite from and aligned with one another and having a first maximum thickness therebetween, and the end wall portion including and extending between a first end portion and a second end portion, the first end portion and the second end portion being at least in part radio opaque, the first end portion and the second end portion being spaced apart from one another, and each of the first end portion and the second end portion having a thickness greater than the remainder of the end wall portion;

contacting an upper wall portion of the spinal implant trial with a lower end portion of the upper vertebral body and contacting a lower wall portion of the spinal implant trial with an upper end portion of the lower vertebral body;

placing the spinal implant trial in a first orientation and a first position within the disc space, a majority of the spinal implant trial being positioned on only one lateral side of the disc space;

producing a first one of at least two first fluoroscopic images from a direct lateral direction of the spinal implant trial in the first orientation and the first position within the disc space;

producing a first one of at least two second fluoroscopic images from an anterior-posterior direction of the spinal implant trial in the first orientation and the first position within the disc space;

adjusting the orientation of the spinal implant trial to place the spinal implant trial in a second orientation so that a first horizontal distance across the first fin in a second one of the at least two first fluoroscopic images from the direct lateral direction approximates the first maximum thickness between the first planar surface and the second planar surface of the first fin; and adjusting the position of the spinal implant trial to place the spinal implant trial in a second position so that the first end portion and the second end portion of the end wall portion are positioned on opposite sides of the a spinous process associated with the upper vertebral body in a second one of the at least two second fluoroscopic images from the anterior-posterior direction.

9. The method of claim 8, further comprising adjusting the orientation of the spinal implant trial so that the first end portion and the second end portion of the end wall portion are overlapped with one another in the second one of the at least two first fluoroscopic images from the direct lateral direction.

10. The method of claim 9, further comprising adjusting the orientation of the spinal implant trial so that a second horizontal distance between the first fin, and the first end portion and the second end portion that are overlapped with one another is maximized in the second one of the at least two first fluoroscopic images from the direct lateral direction.

11. The method of claim 10, further comprising adjusting the orientation of the spinal implant trial so that a third horizontal distance across a second fin interrupting the interior void in the second one of the at least two first fluoroscopic images from the direct lateral direction approximates a second maximum thickness between a third planar surface and a fourth planar surface of the second fin, the third planar surface being in a third plane and the fourth planar surface being in a fourth plane, the third planar surface and the fourth planar surface being opposite from and aligned one another.

12. The method of claim 11, further comprising adjusting the position of the spinal implant trial so that a distal end portion thereof is positioned proximate an anterior portion of the disc space.

13. The method of claim 12, further comprising selecting a spinal implant corresponding to one of a fourth horizontal distance between the first fin, and the first end portion and the second end portion that are overlapped with one another in the second one of the at least two first fluoroscopic images in the direct lateral direction, and a fifth horizontal distance between the second fin, and the first end portion and the second portion that are overlapped with one another in the second one of the at least two first fluoroscopic images in the direct lateral direction.

14. A spinal implant trial comprising:

a proximal first end, a distal second end, a body portion, and a head portion, the body portion extending from the proximal first end to the head portion, and the head portion extending from the body portion to the distal second end, the body portion including a first end collocated with the proximal first end of the spinal implant trial, an opposite second end, a first mid-longitudinal axis extending through the first end and the second end of the body portion, an upper wall portion extending between the first end and the second end of the body portion, a lower wall portion extending between the first end and the second end, a first interior portion formed between the upper wall portion and the lower wall portion of the body portion, a first opening provided on a first lateral side of the body portion between the upper wall portion and the lower wall portion of the body portion and communicating with the first interior portion, a second opening provided on a second lateral side of the body portion between the upper wall portion and the lower wall portion of the body portion and communicating with the first interior portion, and at least a first fin provided in the first interior portion, the first fin being at least in part radio opaque, the first fin having a first planar surface in a first plane and a second planar surface in a second plane, the first planar surface and the second planar surface being opposite from and aligned with one another and having a first maximum thickness therebetween, each of the first planar surface and the second planar surface extending from at least adjacent the upper wall portion of the body portion to at least adjacent the lower wall portion of the body portion, and extending from at least adjacent the first opening to at least adjacent the second opening, the head portion including a first end, an opposite second end collocated with the distal second end of the spinal implant trial, a second mid-longitudinal axis extending through the first end and the second end of the head portion, an upper wall portion extending between the first end and the second end of the head portion, a lower wall portion extending between the first end and the second end of the head portion, a second interior portion communicating with the first interior portion and formed between the upper wall portion and the lower wall portion of the head portion, and an end wall portion positioned at least adjacent the distal second end of the spinal implant trial, the end wall portion including and extending between a first end portion and a second end portion, the first end portion and the second end portion being spaced apart from one another, the first end portion of the end wall portion being positioned proximate the first end of the head portion and the second end portion of the end wall portion being positioned proximate the second end of the head portion, the first end portion and the second end portion of the end wall portion each having a thickness greater than the remainder of the end wall portion and being at least in part radio opaque, the spinal implant trial defining an empty void between the first fin and the end wall portion across the first interior portion and the second interior portion, wherein the spinal implant trial is configured for insertion into a disc space between an upper vertebral body and a lower vertebral body, and after insertion into the disc space, fluoroscopic imagery can be used from a direct lateral direction and an anterior-posterior direction to determine if the spinal implant trial is at least properly oriented and properly positioned with respect to the lateral width of the disc space, the fluoroscopic imagery from the direct lateral direction showing that the spinal implant trial is properly oriented within the disc space when the first end portion and the second end portion are overlapped with one another, when a first horizontal distance across the first fin approximates the first maximum thickness between the first planar surface and the second planar surface of the first fin, and when a second horizontal distance between the first and the first end portion and the second end portion that are overlapped with one another is maximized across the empty void of the first interior portion and the second interior portion, and the fluoroscopic imagery from the anterior-posterior direction showing that the spinal implant trial is properly positioned with respect to the lateral width of the disc space when the first end portion and the second end portion of the end wall portion are positioned on opposite sides of a spinous process associated with the upper vertebral body.

15. The spinal implant trial of claim 14, further comprising a second fin provided in the first interior portion, the second fin being at least in part radio opaque, the second fin being positioned between the first end of the body portion and the first fin, the second fin having a third planar surface in a third plane and a fourth planar surface in a fourth plane, the third planar surface and the fourth planar surface being opposite from and aligned with one another and having a second maximum thickness therebetween, each of the third planar surface and the fourth planar surface extending from at least adjacent the first opening to at least adjacent the second opening, and extending between the upper wall portion and the lower wall portion of the body portion within the first interior space.

16. The spinal implant trial of claim 15, wherein the fluoroscopic imagery from the direct lateral direction further shows that the spinal implant trial is properly oriented within the disc space when a third horizontal distance across the second fin approximates the second maximum thickness between the third planar surface and the fourth planar surface of the second fin.

17. The spinal implant trial of claim 15, wherein, when the spinal implant trial is properly oriented and positioned, the second horizontal distance in the fluoroscopic imagery from the direct lateral direction between the first fin, and the first end portion and the second end portion that are overlapped with one another, and a third horizontal distance in the fluoroscopic imagery from the direct lateral direction between the second fin and the first end portion and the second end portion that are overlapped with one another can be used in selecting a correspondingly sized spinal implant.

18. The spinal implant trial of claim 14, wherein the first mid-longitudinal axis and the second mid-longitudinal axis are transverse to one another, the upper wall portion and the lower wall portion each include a first side surface extending at least partially in a third plane parallel to the first mid-longitudinal axis, and the upper wall portion and the lower wall portion each include a second side surface extending at least partially in a fourth plane parallel to the first mid-longitudinal axis, the body portion residing between the third plane and the fourth plane, and a portion of the head portion being located on an opposite side of the third plane from the body portion.

19. The spinal implant trial of claim 14, further comprising an upper surface extending along the upper wall portion of the body portion and the upper wall portion of the head portion, and a lower surface extending along the lower wall portion of the body portion and the lower wall portion of the head portion, at least a portion of the upper surface contacting a lower endplate of the upper vertebral body and at least portion of the lower surface contacting an upper endplate of the lower vertebral body when the spinal implant trial is inserted into the disc space.

20. The spinal implant trial of claim 14, further comprising a nose portion formed on the head portion at the distal second end of the spinal implant trial, the nose portion including an upper wedge-shaped surface and a lower wedge-shaped surface, the upper wedge-shaped surface and the lower wedge-shaped surface being configured to facilitate entry of the spinal implant trial between the upper vertebral body and the lower vertebral body.

21. A spinal implant trial comprising:

a proximal first end, a distal second end, a body portion, and a head portion, the body portion extending from the proximal first end to the head portion, and the head portion extending from the body portion to the distal second end, the body portion including a first end collocated with the proximal first end of the spinal implant trial, an opposite second end, a first mid-longitudinal axis extending through the first end and the second end of the body portion, an upper wall portion extending between the first end and the second end of the body portion, a lower wall portion extending between the first end and the second end, a first interior portion formed between the upper wall portion and the lower wall portion of the body portion, a first opening provided on a first lateral side of the body portion between the upper wall portion and the lower wall portion of the body portion and communicating with the first interior portion, a second opening provided on a second lateral side of the body portion between the upper wall portion and the lower wall portion of the body portion and communicating with the first interior portion, and at least a first fin provided in the first interior portion, the first fin being at least in part radio opaque, the first fin having a first planar surface in a first plane and a second planar surface in a second plane, the first planar surface and the second planar surface being opposite from one another and having a first maximum thickness therebetween, each of the first planar surface and the second planar surface extending from at least adjacent the upper wall portion of the body portion to at least adjacent the lower wall portion of the body portion, and extending from at least adjacent the first opening to at least adjacent the second opening, the head portion including a first end, an opposite second end collocated with the distal second end of the spinal implant trial, a second mid-longitudinal axis extending through the first end and the second end of the head portion, an upper wall portion extending between the first end and the second end of the head portion, a lower wall portion extending between the first end and the second end of the head portion, a second interior portion communicating with the first interior portion and formed between the upper wall portion and the lower wall portion of the head portion, and an end wall portion positioned at least adjacent the distal second end of the spinal implant trial, the end wall portion including and extending between a first end portion and a second end portion, the first end portion and the second end portion being spaced apart from one another, the first end portion of the end wall portion being positioned proximate the first end of the head portion and the second end portion of the end wall portion being positioned proximate the second end of the head portion, the first end portion and the second end portion of the end wall portion each having a thickness greater than the remainder of the end wall portion and being at least in part radio opaque, the spinal implant trial defining an empty void between the first fin and the end wall portion across the first interior portion and the second interior portion, wherein the spinal implant trial is configured for insertion into a disc space between an upper vertebral body and a lower vertebral body, and after insertion into the disc space, fluoroscopic imagery can be used from a direct lateral direction and an anterior-posterior direction to determine if the spinal implant trial is at least properly oriented and properly positioned with respect to the lateral width of the disc space, the fluoroscopic imagery from the direct lateral direction showing that the spinal implant trial is properly oriented within the disc space when the first end portion and the second end portion overlap one another, when a first horizontal distance across the first fin approximates the first maximum thickness between the first planar surface and the second planar surface of the first fin, and when a second horizontal distance between the first fin, and the first end portion and the second end portion that are overlapped with one another is maximized across the empty void of the first interior portion and the second interior portion, and the fluoroscopic imagery from the anterior-posterior direction showing that the spinal implant trial is properly positioned with respect to the lateral width of the disc space when the first end portion and the second end portion of the end wall portion are positioned on opposite sides of a spinous process associated with the upper vertebral body.

22. The spinal implant trial of claim 21, further comprising a second fin provided in the first interior portion, the second fin being at least in part radio opaque, the second fin being positioned between the first end of the body portion and the first fin, the second fin having a third planar surface in a third plane and a fourth planar surface in a fourth plane, the third planar surface and the fourth planar surface being opposite from one another and having a second maximum thickness therebetween, each of the third planar surface and the fourth planar surface extending from at least adjacent the first opening to at least adjacent the second opening, and extending between the upper wall portion and the lower wall portion of the body portion within the first interior space.

23. The spinal implant trial of claim 22, wherein the fluoroscopic imagery from the direct lateral direction further shows that the spinal implant trial is properly oriented within the disc space when a third horizontal distance across the second fin approximates the second maximum thickness between the third planar surface and the fourth planar surface of the second fin.

24. The spinal implant trial of claim 22, wherein, when the spinal implant trial is properly oriented and positioned, the second horizontal distance in the fluoroscopic imagery from the direct lateral direction between the first fin, and the first end portion and the second end portion that are overlapped with one another, and a third horizontal distance in the fluoroscopic imagery from the direct lateral direction between the second fin and the first end portion and the second end portion that are overlapped with one another can be used in selecting a correspondingly sized spinal implant.

25. The spinal implant trial of claim 21, wherein the first mid-longitudinal axis and the second mid-longitudinal axis are transverse to one another, the upper wall portion and the lower wall portion each include a first side surface extending at least partially in a third plane parallel to the first mid-longitudinal axis, and the upper wall portion and the lower wall portion each include a second side surface extending at least partially in a fourth plane parallel to the first mid-longitudinal axis, the body portion residing between the third plane and the fourth plane, and a portion of the head portion being located on an opposite side of the third plane from the body portion.

26. The spinal implant trial of claim 21, further comprising an upper surface extending along the upper wall portion of the body portion and the upper wall portion of the head portion, and a lower surface extending along the lower wall portion of the body portion and the lower wall portion of the head portion, at least a portion of the upper surface contacting a lower endplate of the upper vertebral body and at least portion of the lower surface contacting an upper endplate of the lower vertebral body when the spinal implant trial is inserted into the disc space.

27. The spinal implant trial of claim 21, further comprising a nose portion formed on the head portion at the distal end second end of the spinal implant trial, the nose portion including an upper wedge-shaped surface and a lower wedge-shaped surface, the upper wedge-shaped surface and the lower wedge-shaped surface being configured to facilitate entry of the spinal implant trial between the upper vertebral body and the lower vertebral body.

* * * * *